United States Patent
Wu et al.

(10) Patent No.: US 12,357,673 B2
(45) Date of Patent: Jul. 15, 2025

(54) COMPOSITIONS COMPRISING ALBUMIN-FMS-LIKE TYROSINE KINASE 3 LIGAND FUSION PROTEINS AND USES THEREOF

(71) Applicant: The Johns Hopkins University, Baltimore, MD (US)

(72) Inventors: T. C. Wu, Stevenson, MD (US); Chien-Fu Hung, Timonium, MD (US); Brandon Lam, Baltimore, MD (US)

(73) Assignee: The Johns Hopkins University

( * ) Notice: Subject to any disclaimer, the term of this patent is extended or adjusted under 35 U.S.C. 154(b) by 0 days.

(21) Appl. No.: 17/561,606

(22) Filed: Dec. 23, 2021

(65) Prior Publication Data

US 2022/0211811 A1 Jul. 7, 2022

Related U.S. Application Data

(62) Division of application No. 16/244,200, filed on Jan. 10, 2019, now Pat. No. 11,246,908.

(60) Provisional application No. 62/615,579, filed on Jan. 10, 2018.

(51) Int. Cl.
| | |
|---|---|
| *C07K 14/475* | (2006.01) |
| *A61K 38/17* | (2006.01) |
| *A61K 38/18* | (2006.01) |
| *A61K 38/19* | (2006.01) |
| *A61K 38/38* | (2006.01) |
| *A61N 5/00* | (2006.01) |
| *A61P 35/00* | (2006.01) |
| *C07K 14/52* | (2006.01) |
| *C07K 14/765* | (2006.01) |
| *C07K 16/28* | (2006.01) |
| *C07K 19/00* | (2006.01) |
| *C12N 15/62* | (2006.01) |
| *A61K 45/06* | (2006.01) |

(52) U.S. Cl.
CPC .......... *A61K 38/1793* (2013.01); *A61K 38/18* (2013.01); *A61K 38/19* (2013.01); *A61K 38/38* (2013.01); *A61N 5/00* (2013.01); *A61P 35/00* (2018.01); *C07K 14/475* (2013.01); *C07K 14/52* (2013.01); *C07K 14/765* (2013.01); *C07K 16/2827* (2013.01); *C07K 19/00* (2013.01); *C12N 15/62* (2013.01); *A61K 45/06* (2013.01); *C07K 2319/31* (2013.01)

(58) Field of Classification Search
CPC ............ C07K 2319/00; C07K 2319/31; C07K 14/475; C07K 14/52; C07K 14/76; C07K 14/765; C07K 19/00; A61K 38/18; A61K 38/19; A61K 38/38

See application file for complete search history.

(56) References Cited

U.S. PATENT DOCUMENTS

| | | | |
|---|---|---|---|
| 6,291,661 B1 | 9/2001 | Graddis et al. | |
| 9,486,519 B2 | 11/2016 | Sahin et al. | |
| 2003/0077263 A1 | 4/2003 | Maraskovsky et al. | |
| 2003/0113341 A1 | 6/2003 | Lynch et al. | |
| 2003/0219875 A1* | 11/2003 | Rosen | A61P 9/10 514/6.9 |
| 2004/0131587 A1* | 7/2004 | Thomas | A61K 38/191 514/19.3 |
| 2006/0063256 A1 | 3/2006 | Norment et al. | |
| 2011/0159023 A1* | 6/2011 | Langermann | A61P 35/00 424/192.1 |
| 2019/0218559 A1* | 7/2019 | Qi | C12N 15/86 |

FOREIGN PATENT DOCUMENTS

| | | |
|---|---|---|
| WO | WO-9857655 A1 * | 12/1998 |
| WO | 2011131944 A1 | 10/2011 |
| WO | 2017099474 A1 | 6/2017 |

OTHER PUBLICATIONS

Anandasabapathy et al. Efficacy and safety of CDX-301, recombinant human Flt3L, at expanding dendritic cells and hematopoietic stem cells in healthy human volunteers. Bone Marrow Transplant 50: 924-930, 2015.*
Bernstein et al. Immunotherapy and stereotactic ablative radiotherapy (ISABR): a curative approach? Nat Rev Clin Oncol 13: 516-524, 2016.*
Chakravarty et al. Flt3-Ligand Administration after Radiation Therapy Prolongs Survival in a Murine model of metastatic lung cancer. Cancer Res 59: 6028-6032, 1999.*
Chakravarty et al. Flt3L Therapy following localized tumor irradiation generates long-term protective immune response in metastastic lung cancer: Its implication in designing a vaccination strategy. Oncology 70: 245-254, 2006.*
Clinical Trial NCT02839265 History of Changes, clinicaltrials.gov, Jul. 18, 2016 (4 total pages).*
Larsen et al. Albumin-based drug delivery: harnessing nature to cure disease. Molec Cell Ther 4:3, 2016; 12 total pages.*
Lynch et al. Flt3 ligand induces tumor regression and antitumor immune responses in vivo. Nature Med 3(7): 625-631, 1997.*
Graddis et al. Structure-function analysis of Flt3 ligand-FLT3 receptor interactions using a rapid functional screen. J Biol Chem 273(28): 17626-17633, 1998.*
Genbank Accession No. NP_001450; Dec. 24, 2022 (3 total pages).*
Genbank Accession XP_008921.1, Oct. 16, 2001 (1 page).*
Medina et al. PD-1 pathway inhibitors: immuno-oncology agents for restoring antitumor immune responses. Pharmacotherapy 36(3): 317-334, 2016.*

(Continued)

*Primary Examiner* — Bridget E Bunner
(74) *Attorney, Agent, or Firm* — Fox Rothschild LLP

(57) ABSTRACT

The present invention provides a novel fusion protein of Flt3L and albumin and its use to increase the Flt3L half-life in vivo and to deliver Flt3L to immune cells in a subject to enhance alternative dendritic cell populations. Use of the fusion protein in combination with other chemotherapeutic, radiotherapeutic and immunotherapeutic methods are also provided.

20 Claims, 13 Drawing Sheets

Specification includes a Sequence Listing.

(56) References Cited

OTHER PUBLICATIONS

Mwangi et al. Identification of fetal liver tyrosine kinase 3 (Flt3) ligand domain required for receptor binding and function using naturally occurring ligand isoforms. J Immunol 165: 6966-6974, 2000.*
Robinson et al. Delivery of Flt3 ligand (Flt3L) using a poloxamer-based formulation increases biological activity in mice. Bone Marrow Transplant 31: 361-369, 2003.*
Savvides et al. Flt3L ligand structure and unexpected commonalities of helical bundles and cystine knots. Nat Struct Biol 7(6): 486-491, 2000.*
Sleep, D. Albumin and its application in drug delivery. Exp Opin Drug Delivery 12(5): 793-812, 2015.*
Kim et al. Clearance of persistent HPV infection and cervical lesion by therapeutic DNA vaccine in CIN3 patients. Nature Comm 5: 5317, 2014 (14 total pages).*
Schuh et al. Flt3L-induced anti-tumor activity in vivo. Vet Pathol 34(5): 496, 1997 (1 page).*
Zhang et al. Human Flt3 Ligand from Pichia pastoris inhibits growth of lymphoma and colon adenocarcinoma in mice. J Exp Therapeutics Oncol 5: 161-166, 2006.*
Zurkova et al. The expression of the soluble isoform of hFlt3 ligand by recombinant vaccinia virus enhances immunogenicity of the vector. Oncol Reports 21: 1335-1343, 2009.*
Topalian et al., (2015). Immune checkpoint blockade: a common denominator approach to cancer therapy. Cancer Cell. Apr. 13, 2015;27(4):450-61.
Takamori et al., (2017) Combination Therapy of Radiotherapy and Anti-PD-1/PD-L1 Treatment in Non-Small-cell Lung Cancer: A Mini-review. Clin Lung Cancer. Jul. 6, 2017. pii: S1525-7304(17)30202-4.
Hellmann et al., (2016) Combinatorial Cancer Immunotherapies. Adv Immunol. 2016; 130:251-77.
Lee et al., (2015) Local administration of granulocyte macrophage colony-stimulating factor induces local accumulation of dendritic cells and antigen-specific CD8+ T cells and enhances dendritic cell cross-presentation. Vaccine. Mar. 24, 2015;33(13):1549-55.
Dranoff et al., (1993) Vaccination with irradiated tumor cells engineered to secrete murine granulocyte-macrophage colony-stimulating factor stimulates potent, specific, and long lasting anti-tumor immunity. Proc Natl Acad Sci USA. Apr. 15, 1993;90(8):3539-43.
Belz et al., (2012) Transcriptional programming of the dendritic cell network. Nat Rev Immunol. Jan. 25, 2012;12(2):101-13.
Gardner et al., (2016). Dendritic Cells and Cancer Immunity. Trends Immunol. Dec. 2016;37(12):855-865.
Gibbons et al., (2017) Functional Expression of Programmed Death-Ligand 1 (B7-H1) by Immune Cells and Tumor Cells. Front Immunol. Aug. 10, 2017;8:961.
Pulendran et al., (1999) Distinct dendritic cell subsets differentially regulate the class of immune response in vivo. Proc Natl Acad Sci USA. Feb. 2, 1999;96(3):1036-41.
Salmon et al., (2016) Expansion and Activation of CD103(+) Dendritic Cell Progenitors at the Tumor Site Enhances Tumor Responses to Therapeutic PD-L1 and BRAF Inhibition. Immunity. Apr. 19, 2016;44(4):924-38.
Schmidt et al., (2017) Direct demonstration of a neonatal Fc receptor (FcRn)-driven endosomal sorting pathway for cellular recycling of albumin. J Biol Chem. Aug. 11, 2017;292(32):13312-13322.
Wang et al., (2015) In vivo albumin labeling and lymphatic imaging. Proc Natl Acad Sci USA. Jan. 6, 2015;112(1):208-13.
Inaba et al., (1992) Generation of large Nos. of dendritic cells from mouse bone marrow cultures supplemented with granulocyte/macrophage colony-stimulating factor. J Exp Med. Dec. 1, 1992;176(6):1693-702.
Lin et al., (1996) Treatment of established tumors with a novel vaccine that enhances major histocompatibility class II presentation of tumor antigen. Cancer Res. Jan. 1, 1996;56(1):21-6.
Stadler et al., Telomere position effect regulates DUX4 in human facioscapulohumeral muscular dystrophy., Nat Struct Mol Biol (2013), 20(6):671-8.
Homma et al., A unique library of myogenic cells from facioscapulohumeral muscular dystrophy subjects and unaffected relatives: family, disease and cell function., European Journal of Human Genetics (2012). 20(4):404-10.
Reber et al., Flt3 ligand bioactivity and pharmacology in neoplasia., Curr Drug Targets Immune Endocr Metabol Disord. 2004., 4(2):14-56.
Morse et al., Preoperative mobilization of circulating dendritic cells by Flt3 ligand administration to patients with metastatic colon cancer., (2000) Journal of Clinical Oncology 18:3883-3893.
Kreiter et al., FLT3 ligand enhances the cancer therapeutic potency of naked RNA vaccines., Cancer Research , 2011, 71(19):6132.
Swee et al., Expansion of peripheral naturally occurring T regulatory cells by Fms-like tyrosine kinase 3 ligand treatment., (2009) Blood 113(25):6277.
Mosca et al., Multiple signals are required for maturation of human dendritic cells mobilized in vivo with Flt3 ligand., (2002) Journal of Leukocyte Biology 72, 546.
McNeel et al., Pilot study of an HLA-A2 peptide vaccine using flt3 ligand as a systemic vaccine adjuvant., Journal of Clinical Immunology 2003, 23(1):62-72.
Branca., Rekindling cancer vaccines., Nature Biotechnology 2016, 23(10):1019.

* cited by examiner

FIGURES 1A-1C

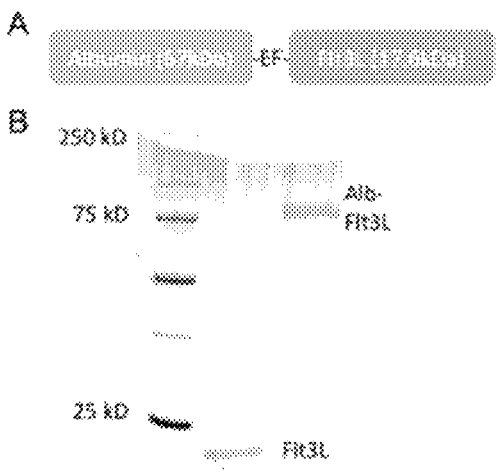

C

Human albumin (NM_000477)-Human Flt3 ligand (AAA90950.1):
MKWVTFISLLFLFSSAYSRGVFRRDAHKSEVAHRFKDLGEENFKALVLIA
FAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTA
FHDNEETFLKKYLYEIARRHPYFYAPELLFFAKRYKAAFTECCQAADKAA
CLLPKLDELRDEGKASSAKQRLKCASLQKFGERAFKAWAVARLSQRFPKA
EFAEVSKLVTDLTKVHTECCHGDLLECADDRADLAKYICENQDSISSKLK
ECCEKPLLEKSHCIAEVENDEMPADLPSLAADFVESKDVCKNYAEAKDVF
LGMFLYEYARRHPDYSVVLLLRLAKTYETTLEKCCAAADPHECYAKVFDE
FKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKC
CTESLVNRRPCFSALEVDETYVPKEFNAETFTFHADICTLSEKERQIKKQ
TALVELVKHKPKATKEQLKAVMDDFAAFVEKCCKADDKETCFAEEGKKLV
AASQAALGLEFTQDCSFQHSPISSDFAVKIRELSDYLLQDYPVTVASNLQ
DEELCGGLWRLVLAQRWMERLKTVAGSKMQGLLERVNTEIHFVTKCAFQP
PPSCLRFVQTNISRLLQETSEQLVALKPWITRQNFSRCLELQCQPVETVF
HRVSQDGLDLLTS (SEQ ID NO: 1)

Mouse albumin (NM_009654)- Human Flt3 ligand (AAA90950.1):
MKWVTFLLLLLFVSGSAFSRGVFRREAHKSEIAHRYNDLGEQHFKGLVLIA
FSQYLQKCSYDEHAKLVQEVTDFAKTCVADESAANCDKSLHTLFGDKLCA
IPNLRENYGELADCCTKQEPERNECFLQHKDDNPSLPPFERPEAEAMCTS
FKENPTTFMGHYLHEVARRHPYFYAPELLYYAEQYNEILTQCCAEADKES
CLTPKLDGVKEKALVSSVRQRMKCSSMQKFGERAFKAWAVARLSQTFPNA
DFAEITKLATDLTKVNKECCHGDLLECADDRAELAKYMCENQATISSKLQ
TCCDKPLLKKAHCLSEVEHDTMPADLPAIAADFVEDQEVCKNYAEAKDVF
LGTFLYEYSRRHPDYSVSLLLRLAKKYEATLEKCCAEANPPACYGTVLAE
FQPLVEEPKNLVKTNCDLYEKLGEYGFQNAILVRYTQKAPQVSTPTLVEA
ARNLGRVGTKCCTLPEDQRLPCVEDYLSAILNRVCLLHEKTPVSEHVTKC
CSGSLVERRPCFSALTVDETYVPKEFKAETFTFHSDICTLPEKEKQIKKQ
TALAELVKHKPKATAEQLKTVMDDFAQFLDTCCKAADKDTCFSTEGPNLV
TRCKDALAEFTQDCSFQHSPISSDFAVKIRELSDYLLQDYPVTVASNLQD
EELCGGLWRLVLAQRWMERLKTVAGSKMQGLLERVNTEIHFVTKCAFQPP
PSCLRPVQTNISRLLQETSEQLVALKPWITRQNFSRCLELQCQPVETVFH
RVSQDGLDLLTS
(SEQ ID NO: 2)

E

Mouse albumin (NM_009654)-Mouse Flt3 ligand (EDL22813.1):
MKWVTFLLLLLFVSGSAFSRGVFRREAHKSEIAHRYNDLGEQHFKGLVLIA
FSQYLQKCSYDEHAKLVQEVTDFAKTCVADESAANCDKSLHTLFGDKLCA
IPNLRENYGELADCCTKQEPERNECFLQHKDDNPSLPPFERPEAEAMCTS
FKENPTTFMGHYLHEVARRHPYFYAPELLYYAEQYNEILTQCCAEADKES
CLTPKLDGVKEKALVSSVRQRMKCSSMQKFGERAFKAWAVARLSQTFPNA
DFAEITKLATDLTKVNKECCHGDLLECADDRAELAKYMCENQATISSKLQ
TCCDKPLLKKAHCLSEVEHDTMPADLPAIAADFVEDQEVCKNYAEAKDVF
LGTFLYEYSRRHPDYSVSLLLRLAKKYEATLEKCCAEANPPACYGTVLAE
FQPLVEEPKNLVKTNCDLYEKLGEYGFQNAILVRYTQKAPQVSTPTLVEA
ARNLGRVGTKCCTLPEDQRLPCVEDYLSAILNRVCLLHEKTPVSEHVTKC
CSGSLVERRPCFSALTVDETYVPKEFKAETFTFHSDICTLPEKEKQIKKQ
TALAELVKHKPKATAEQLKTVMDDFAQFLDTCCKAADKDTCFSTEGPNLV
TRCKDALAEFMTVLAPAWSPNSSLLLLLLLLSPCLRGTPDCYFSHSPISS
NFKVKFRELTDHLLKDYPVTVAVNLQDEKHCKALWSLFLAQRWTEQLKTV
AGSKMQTLLEDVNTEIHFVTSCTFQPLPECLRFVQTNISHLLKDTCTQLL
ALKPCIGKACQNFSRCLEVQCQPDSSTLLPPRSPIALEATELPEPRPRQL
LLLLLLLLPLTLVLLAAAWGLRWQRARRRGELHPGVPLPSHP
(SEQ ID NO: 3)

FIGURE 4B

|  | Day 0 | Day 7 | Day 14 |
|---|---|---|---|
| E7 + MPL | ↑ E7 Peptide (5 ug IV) + MPL (10 ug SC) | ↑ E7 Peptide (5 ug IV) + MPL (10 ug SC) | ↑ |
| E7 + MPL + Flt3L | ↑ E7 Peptide (5 ug IV) + MPL (10 ug SC) + Flt3L (10 ug IV) | ↑ E7 Peptide (5 ug IV) + MPL (10 ug SC) + Flt3L (10 ug IV) | ↑ |
| E7 + MPL + Alb-Flt3L | ↑ E7 Peptide (5 ug IV) + MPL (10 ug SC) + Alb-Flt3L (50 ug IV) | ↑ E7 Peptide (5 ug IV) + MPL (10 ug SC) + Alb-Flt3L (50 ug IV) | ↑ |
| E7 + Flt3L | ↑ E7 Peptide (5ug IV) + Flt3L (10 ug IV) | ↑ E7 Peptide (5ug IV) + Flt3L (10 ug IV) | ↑ |
| E7 + Alb-Flt3L | ↑ E7 Peptide (5ug IV) + Alb-Flt3L (50 ug IV) | ↑ E7 Peptide (5ug IV) + Alb-Flt3L (50 ug IV) | ↑ |
| E7 | ↑ E7 Peptide (5 ug IV) | ↑ E7 Peptide (5 ug IV) | ↑ |

SEQUENCE LISTING

<160> NUMBER OF SEQ ID NOS: 9

<210> SEQ ID NO 1
<211> LENGTH: 763
<212> TYPE: PRT
<213> ORGANISM: Artificial Sequence
<220> FEATURE:
<223> OTHER INFORMATION: synthetic sequence

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

-continued

```
Glu Ser Ala Glu Asn Cys Asp Lys Ser Leu His Thr Leu Phe Gly Asp
                85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
            115                 120                 125
His Lys Asp Asp Asn Pro Asn Leu Pro Arg Leu Val Arg Pro Glu Val
        130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
            180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Gln Arg Leu Lys Cys
        210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
            275                 280                 285
Cys Glu Asn Gln Asp Ser Ile Ser Ser Lys Leu Lys Glu Cys Cys Glu
        290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
            355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
            435                 440                 445
Glu Val Ser Arg Asn Leu Gly Lys Val Gly Ser Lys Cys Cys Lys His
        450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
```

```
                500             505             510
Ser Ala Leu Glu Val Asp Glu Thr Tyr Val Pro Lys Glu Phe Asn Ala
            515                 520                 525
Glu Thr Phe Thr Phe His Ala Asp Ile Cys Thr Leu Ser Glu Lys Glu
            530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
            565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
            595                 600                 605
Leu Glu Phe Thr Gln Asp Cys Ser Phe Gln His Ser Pro Ile Ser Ser
            610                 615                 620
Asp Phe Ala Val Lys Ile Arg Glu Leu Ser Asp Tyr Leu Leu Gln Asp
625                 630                 635                 640
Tyr Pro Val Thr Val Ala Ser Asn Leu Gln Asp Glu Glu Leu Cys Gly
            645                 650                 655
Gly Leu Trp Arg Leu Val Leu Ala Gln Arg Trp Met Glu Arg Leu Lys
            660                 665                 670
Thr Val Ala Gly Ser Lys Met Gln Gly Leu Leu Glu Arg Val Asn Thr
            675                 680                 685
Glu Ile His Phe Val Thr Lys Cys Ala Phe Gln Pro Pro Ser Cys
            690                 695                 700
Leu Arg Phe Val Gln Thr Asn Ile Ser Arg Leu Leu Gln Glu Thr Ser
705                 710                 715                 720
Glu Gln Leu Val Ala Leu Lys Pro Trp Ile Thr Arg Gln Asn Phe Ser
            725                 730                 735
Arg Cys Leu Glu Leu Gln Cys Gln Pro Val Glu Thr Val Phe His Arg
            740                 745                 750
Val Ser Gln Asp Gly Leu Asp Leu Leu Thr Ser
            755                 760

<210> SEQ ID NO 2
<211> LENGTH: 762
<212> TYPE: PRT
<213> ORGANISM: Artificial Sequence
<220> FEATURE:
<223> OTHER INFORMATION: synthetic sequence

<400> SEQUENCE: 2

Met Lys Trp Val Thr Phe Leu Leu Leu Leu Phe Val Ser Gly Ser Ala
1               5                   10                  15
Phe Ser Arg Gly Val Phe Arg Arg Glu Ala His Lys Ser Glu Ile Ala
            20                  25                  30
His Arg Tyr Asn Asp Leu Gly Glu Gln His Phe Lys Gly Leu Val Leu
            35                  40                  45
Ile Ala Phe Ser Gln Tyr Leu Gln Lys Cys Ser Tyr Asp Glu His Ala
            50                  55                  60
Lys Leu Val Gln Glu Val Thr Asp Phe Ala Lys Thr Cys Val Ala Asp
65                  70                  75                  80
Glu Ser Ala Ala Asn Cys Asp Lys Ser Leu His Thr Leu Phe Gly Asp
            85                  90                  95
Lys Leu Cys Ala Ile Pro Asn Leu Arg Glu Asn Tyr Gly Glu Leu Ala
```

```
                100                 105                 110
Asp Cys Cys Thr Lys Gln Glu Pro Glu Arg Asn Glu Cys Phe Leu Gln
            115                 120                 125

His Lys Asp Asp Asn Pro Ser Leu Pro Pro Phe Glu Arg Pro Glu Ala
130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
            165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gln Arg Met Lys Cys
            210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
            245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
            275                 280                 285

Cys Glu Asn Gln Ala Thr Ile Ser Ser Lys Leu Gln Thr Cys Cys Asp
            290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
            325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
            370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
            405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
            435                 440                 445

Glu Ala Ala Arg Asn Leu Gly Arg Val Gly Thr Lys Cys Cys Thr Leu
            450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
            485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
            515                 520                 525
```

Glu Thr Phe Thr Phe His Ser Asp Ile Cys Thr Leu Pro Glu Lys Glu
    530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
            565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

Glu Phe Thr Gln Asp Cys Ser Phe Gln His Ser Pro Ile Ser Ser Asp
    610                 615                 620

Phe Ala Val Lys Ile Arg Glu Leu Ser Asp Tyr Leu Leu Gln Asp Tyr
625                 630                 635                 640

Pro Val Thr Val Ala Ser Asn Leu Gln Asp Glu Glu Leu Cys Gly Gly
            645                 650                 655

Leu Trp Arg Leu Val Leu Ala Gln Arg Trp Met Glu Arg Leu Lys Thr
            660                 665                 670

Val Ala Gly Ser Lys Met Gln Gly Leu Leu Glu Arg Val Asn Thr Glu
        675                 680                 685

Ile His Phe Val Thr Lys Cys Ala Phe Gln Pro Pro Pro Ser Cys Leu
    690                 695                 700

Arg Phe Val Gln Thr Asn Ile Ser Arg Leu Leu Gln Glu Thr Ser Glu
705                 710                 715                 720

Gln Leu Val Ala Leu Lys Pro Trp Ile Thr Arg Gln Asn Phe Ser Arg
            725                 730                 735

Cys Leu Glu Leu Gln Cys Gln Pro Val Glu Thr Val Phe His Arg Val
            740                 745                 750

Ser Gln Asp Gly Leu Asp Leu Leu Thr Ser
        755                 760

<210> SEQ ID NO 3
<211> LENGTH: 773
<212> TYPE: PRT
<213> ORGANISM: Artificial Sequence
<220> FEATURE:
<223> OTHER INFORMATION: synthetic sequence

<400> SEQUENCE: 3

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
            85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

```
His Lys Asp Asp Asn Pro Ser Leu Pro Pro Phe Glu Arg Pro Glu Ala
        130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
            165                 170                 175

Glu Leu Leu Tyr Tyr Ala Glu Gln Tyr Asn Glu Ile Leu Thr Gln Cys
                180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
                260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
        370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
530                 535                 540
```

```
Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

Glu Phe Gly Thr Pro Asp Cys Tyr Phe Ser His Ser Pro Ile Ser Ser
    610                 615                 620

Asn Phe Lys Val Lys Phe Arg Glu Leu Thr Asp His Leu Leu Lys Asp
625                 630                 635                 640

Tyr Pro Val Thr Val Ala Val Asn Leu Gln Asp Glu Lys His Cys Lys
                645                 650                 655

Ala Leu Trp Ser Leu Phe Leu Ala Gln Arg Trp Ile Glu Gln Leu Lys
            660                 665                 670

Thr Val Ala Gly Ser Lys Met Gln Thr Leu Leu Glu Asp Val Asn Thr
        675                 680                 685

Glu Ile His Phe Val Thr Ser Cys Thr Phe Gln Pro Leu Pro Glu Cys
    690                 695                 700

Leu Arg Phe Val Gln Thr Asn Ile Ser His Leu Leu Lys Asp Thr Cys
705                 710                 715                 720

Thr Gln Leu Leu Ala Leu Lys Pro Cys Ile Gly Lys Ala Cys Gln Asn
                725                 730                 735

Phe Ser Arg Cys Leu Glu Val Gln Cys Gln Pro Asp Ser Ser Thr Leu
            740                 745                 750

Leu Pro Pro Arg Ser Pro Ile Ala Leu Glu Ala Thr Glu Leu Pro Glu
        755                 760                 765

Pro Arg Pro Arg Gln
        770

<210> SEQ ID NO 4
<211> LENGTH: 33
<212> TYPE: DNA
<213> ORGANISM: Artificial Sequence
<220> FEATURE:
<223> OTHER INFORMATION: synthetic sequence

<400> SEQUENCE: 4
aaatctagag ccaccatgaa gtgggtaacc ttt                                    33

<210> SEQ ID NO 5
<211> LENGTH: 29
<212> TYPE: DNA
<213> ORGANISM: Artificial Sequence
<220> FEATURE:
<223> OTHER INFORMATION: synthetic sequence

<400> SEQUENCE: 5
tttgaattcg gctaaggcgt ctttgcatc                                        29

<210> SEQ ID NO 6
<211> LENGTH: 33
<212> TYPE: DNA
<213> ORGANISM: Artificial Sequence
<220> FEATURE:
<223> OTHER INFORMATION: synthetic sequence

<400> SEQUENCE: 6
```

```
aaactcgagg ccaccatgaa gtgggtaacc ttt                                     33

<210> SEQ ID NO 7
<211> LENGTH: 29
<212> TYPE: DNA
<213> ORGANISM: Artificial Sequence
<220> FEATURE:
<223> OTHER INFORMATION: synthetic sequence

<400> SEQUENCE: 7
tttgaattct aagcctaagg cagcttgac                                          29

<210> SEQ ID NO 8
<211> LENGTH: 30
<212> TYPE: DNA
<213> ORGANISM: Artificial Sequence
<220> FEATURE:
<223> OTHER INFORMATION: synthetic sequence

<400> SEQUENCE: 8
tttgaattcg ggacacctga ctgttacttc                                         30

<210> SEQ ID NO 9
<211> LENGTH: 33
<212> TYPE: DNA
<213> ORGANISM: Artificial Sequence
<220> FEATURE:
<223> OTHER INFORMATION: synthetic sequence

<400> SEQUENCE: 9
aaacttaagc tactgcctgg gccgaggctc tgg                                     33
```

COMPOSITIONS COMPRISING ALBUMIN-FMS-LIKE TYROSINE KINASE 3 LIGAND FUSION PROTEINS AND USES THEREOF

REFERENCE TO RELATED APPLICATIONS

This application is a Divisional of U.S. application Ser. No. 16/244,200, filed Jan. 10, 2019, which claims priority to, and the benefit under 35 U.S.C. § 119(e) of U.S. Provisional Application No. 62/615,579, filed Jan. 10, 2018. The entire contents of which are incorporated herein by reference in their entirety.

STATEMENT OF GOVERNMENTAL INTEREST

This invention was made with government support under grant nos. CA114425, CA234516 and CA236051 awarded by the National Institutes of Health. The government has certain rights in the invention

INCORPORATION-BY-REFERENCE OF MATERIAL SUBMITTED ELECTRONICALLY

The contents of the sequence listing text file named "048317-621D01US_Sequence_Listing_ST25.txt", which was created on Jan. 9, 2018 and is 21,290 bytes in size, is hereby incorporated by reference in its entirety

BACKGROUND OF THE INVENTION

Immunotherapy has emerged as a promising strategy to treat various cancers. Generally, cancer immunotherapy can be divided into two classes including passive immunotherapy where lab derived molecules such as antibodies specific to tumor antigens are administered and can directly impede progression of the tumor, or active immunotherapy where molecules are administered that mobilize host immune cells to recognize and kill the tumor. Checkpoint blockade such as anti-PD-1/PD-L1 and anti-CTLA-4, which are forms of active immunotherapy, have made breakthrough advances in the last decade and greatly improved the prognosis of many cancer types such as melanoma (1).

Combining these novel checkpoint blockade molecules with traditional strategies to treat cancers including surgical resection, radiation therapy, and chemotherapy have also been shown to improve overall outcome (2).

Most checkpoint blockade strategies function by removing the brakes on the T cells so that they can respond to tumor antigens (3). One significant drawback of this strategy is that it relies on proper presentation of tumor antigens by antigen presenting cells. In the absence of tumor antigen presentation, T cells restored by checkpoint blockade cannot become activated and respond to the tumor. To address this, strategies have been designed to boost antigen presenting cells. Granulocyte macrophage colony-stimulating factor (GM-CSF) is a cytokine responsible for the development of conventional dendritic cell subsets from the bone marrow (4). Conventional dendritic cells are known to be potent antigen presenting cells. Administration of GM-CSF as a tumor therapeutic strategy to enhance conventional dendritic cells has been shown to improved immune responses to tumors and reduce overall tumor burden (5).

While GM-CSF sufficiently develops conventional dendritic cells, there are many other dendritic cell subsets that differ functionally and could be instrumental in recognizing and responding to tumors. Alternative dendritic cell subsets comprise of many cells, including CD8+ dendritic cells, and plasmacytoid dendritic cells (6). Of their many functions, one of importance to tumor immunology is the ability to cross present antigen. Cross presentation involves the uptake of exogenous antigens that would typically be processed and presented in the canonical MHCII pathway, and transferring these antigens to MHCI processing pathways and subsequent presentation on MHCI to prime CD8+ T cells (7). In the context of tumor responses, cross presentation is crucial since exogenous antigens presented on MHCII will engage CD4+ T helper cells and not CD8+ cytotoxic T cells. While T helper cells produce soluble factors that can recruit other immune cells to respond to tumors, cytotoxic T cells have the potent ability to engage and secrete molecules to directly kill tumor cells (8).

Progenitor cells can be skewed to alternative dendritic cells subsets in response to the cytokine FMS-like tyrosine kinase 3 ligand (Flt3L) (6). It has been shown that administration of Flt3L can induce Th1 responses and subsequent B cell responses (9) as well as antitumor immunity (10). Translationally, one draw-back of Flt3L treatment is the need for daily injections due to its short half-life in vivo.

Radiation therapy has been long regarded as a directly cytotoxic cancer treatment and is known to be an effective means of reducing tumor bulk. More recent evidence, however, also shows that radiation is able to counteract the immunosuppressive tumor microenvironment to generate an immune response through mechanisms, such as increased MHC class I expression, presentation of normally suppressed carcinoma-associated antigens, increased expression of pro-inflammatory cytokines, and downregulation of the Fas ligand.

Accordingly, radiation treatment is effective in priming the immune system with cancer antigens. Current radiation strategies, however, have limitations. For example, current radiation paradigms radiate a significant margin to include infiltrating cells. This paradigm requires radiating patients for weeks and, as a result, patients have experienced radiation-associated toxicities, including a drop in the white blood cell (WBC) count, which is counterproductive for immunotherapy. In contrast, focused radiation, such as Stereotactic radiosurgery (SRS), allows for a therapeutic dose of radiation while minimizing radiation-associated toxicities. Further, a high dose of radiation can be delivered over one day with SRS.

As such, there still exists a need for compositions and therapies that increase alternative dendritic cells subsets in combination with checkpoint blockade molecules and traditional strategies to treat cancers including surgical resection, radiation therapy, and chemotherapy to improve overall outcomes.

SUMMARY OF THE INVENTION

The present inventors created a novel fusion protein of Flt3L and albumin as a method to increase the cytokines half-life. Albumin is ubiquitous in the body and known to increase the half-life of molecules it is associated with by binding to the neonatal Fc receptor (FCRN) (11). Through interaction with the FCRN, albumin is believed to traffic through the lymphatic system (12). These properties make albumin a prime candidate to deliver Flt3L in vivo and enhance alternative dendritic cell populations.

In accordance with an embodiment, the present invention provides a composition comprising a fusion polypeptide encoding albumin protein linked to a polypeptide encoding FMS-like tyrosine kinase 3 ligand (Flt3L) protein.

In accordance with an embodiment, the present invention provides a composition comprising a fusion polypeptide encoding human albumin protein linked to a polypeptide encoding human Flt3L protein.

In accordance with an embodiment, the present invention provides a composition comprising a fusion polypeptide encoding murine albumin protein linked to a polypeptide encoding murine Flt3L protein.

In accordance with an embodiment, the present invention provides a composition comprising a fusion polypeptide encoding murine albumin protein linked to a polypeptide encoding human Flt3L protein.

In accordance with an embodiment, the present invention provides a composition comprising a fusion polypeptide encoding human albumin protein linked to a polypeptide encoding murine Flt3L protein.

In accordance with an embodiment, the present invention provides a method of treating cancer in a subject in need thereof, comprising administering to the subject an effective amount of a composition comprising a fusion polypeptide encoding albumin protein linked to a polypeptide encoding Flt3L protein.

In accordance with an embodiment, the present invention provides a method of treating cancer in a subject in need thereof, comprising administering to the subject an effective amount of a composition comprising a fusion polypeptide encoding albumin protein linked to a polypeptide encoding Flt3L protein and an effective amount of at least one additional chemotherapeutic agent.

In accordance with an embodiment, the present invention provides a method of treating cancer in a subject in need thereof, comprising administering to the subject an effective amount of a composition comprising a fusion polypeptide encoding albumin protein linked to a polypeptide encoding Flt3L protein and administering to the subject radiation therapy.

In accordance with an embodiment, the present invention provides a method of treating cancer in a subject in need thereof, comprising administering to the subject an effective amount of a composition comprising a fusion polypeptide encoding albumin protein linked to a polypeptide encoding Flt3L protein and an effective amount of at least one PD-1 inhibiting agent.

BRIEF DESCRIPTION OF THE DRAWINGS

FIGS. 1A-1E depict schematic representation and purity of Albumin-Flt3L fusion protein. 1A) Model of Alb-Flt3L fusion protein. EF residues from cloning site. 1B) SDS-page gel showing molecular weight and purity of Alb-Flt3L. 1C) Sequence of human albumin-human Flt3L. 1D) Sequence of mouse albumin-human Flt3L. 1E) Sequence of mouse albumin-mouse Flt3L FIGS. 2A-2D. Alb-Flt3L retains biological function, expanding cross-presenting DCs in vitro. Bone marrow cells from C57/B6 mice were cultured with 20 ng/ml GM-CSF, 100 ng/ml Flt3L, or 500 ng/ml Alb-Flt3L (Alb-Flt3L is approximately 5× molecular weight of Flt3L). 2A) Flow cytometry plots showing DC development and expansion after 7 day in vitro culture with GM-CSF (20 ng/ml), Flt3L (100 ng/ml), or Alb-Flt3L (500 ng/ml) (Note: M.W. Alb-Flt3L ~5×Flt3L). 2B)-2D) Bar charts summarizing DC development shown in A.

FIG. 4B is a schematic depicting experimental design including injection conditions and schedule of injections of E7 peptide vaccination and Alb-Flt3L injection in C57/B6 mice.

DETAILED DESCRIPTION OF THE INVENTION

Figures 2A, 2B, 2C, 2D:
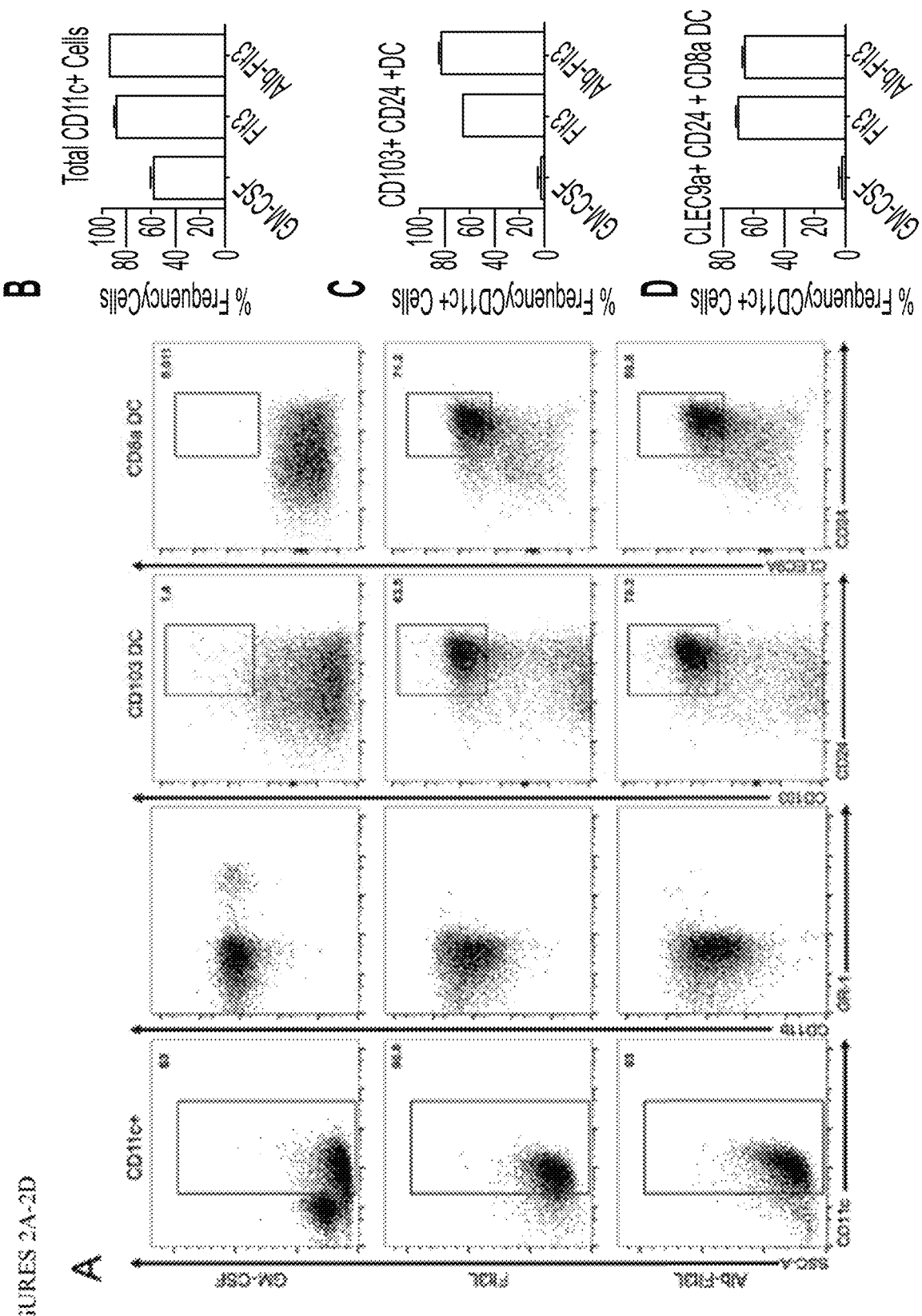

In accordance with one or more embodiments of the present invention, the therapeutic potential of the inventive fusion polypeptide composition comprising albumin conjugated to Flt3L (Alb-Flt3L) to modulate immune cell phenotypes and improve anti-tumor responses with minimal injections is demonstrated. The present inventors now show that the inventive Alb-Flt3L composition retains similar biological activity compared to Flt3L alone, in vitro, and outperforms Flt3L at generating alternative dendritic cells in vivo, by potentially preferentially accumulating in the draining lymph nodes. Additionally, the inventive Alb-Flt3L composition generates potent antigen specific T and B cell responses to OVA and HPV protein E7 antigens. Furthermore, treatment of HPV associated TC-1 tumors with the inventive Alb-Flt3L composition in combination with targeted local radiation therapy results in a significant reduction tumor burden as well as improved overall survival.

Therefore, in accordance with an embodiment, the present invention provides a composition comprising a fusion polypeptide encoding albumin protein linked to a polypeptide encoding FMS-like tyrosine kinase 3 ligand (Flt3L) protein.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises a polypeptide encoding albumin protein, and the second domain comprising a polypeptide encoding FMS-like tyrosine kinase 3 ligand (Flt3L) protein, such as, for example the Human Flt3 ligand (Genbank No. AAA90950.1), or in another embodiment, the Mouse Flt3 ligand (Genbank No. EDL22813.1). Other species of Flt3L peptides are contemplated within the scope of the invention. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means.

As used herein, the term "albumin protein" means the full-length expressed polypeptide of the nucleic acid encoding the albumin gene, or a functional portion or fragment, or variant thereof.

It will be understood by those of ordinary skill in the art that many different isoforms of both human and murine albumin protein exist, and can be used in the compositions disclosed herein. Examples of albumin isoforms include, but are not limited to, human albumin isoforms (NM_000477, AAH41789.1, and AAH35969), for example and mouse albumin ligand isoform (AAH49971), for example.

The term "functional portion or fragment thereof," with respect to the albumin protein, means that the portion or fragment of the albumin polypeptide retains its ability to bind to the neonatal Fc receptor and traffic through the lymphatic system.

In some embodiments, the albumin protein is mammalian. In certain embodiments, the albumin protein can be murine, porcine, ovine, bovine, human, or combinations thereof.

As used herein, the term "Flt3L protein" means the full-length expressed polypeptide of the nucleic acid encoding the FMS-like tyrosine kinase 3 ligand protein gene, or a functional portion or fragment, or variant thereof. The term "functional portion or fragment thereof," with respect to the Flt3L protein, means that the portion or fragment of the Flt3L polypeptide retains its ability to make progenitor cells skewed to alternative dendritic cells subsets, and induce T cell responses and B cell responses in a subject. It will be understood by those of ordinary skill in the art that many different isoforms of both human and murine Flt3L protein exist, and can be used in the compositions disclosed herein. Examples of Flt3L isoforms include, but are not limited to, Human Flt3 ligand isoforms (AAA90950.1, NM_001459.3, and NM_001278637.1), for example and mouse Flt3 ligand isoforms (EDL22813.1, S43291, and AAA90952), for example.

The term "variants" as used herein, means that the wild type amino acid sequences comprising the polypeptides of the compositions, may include substituted amino acids.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," as used herein, includes a sequence of from four to sixteen amino acid residues in which the α-carboxyl group of one amino acid is joined by an amide bond to the main chain (α- or β-) amino group of the adjacent amino acid. The peptides provided herein for use in the described and claimed methods and compositions can be cyclic.

In reference to the fusion polypeptide composition of the present invention, the functional portion can comprise, for instance, about 90%, 95%, or more, of the albumin and/or Flt3L polypeptide.

The functional portion of the fusion polypeptide composition of the present invention can comprise additional amino acids at the amino or carboxy terminus of the portion, or at both termini, which additional amino acids are not found in the amino acid sequence of either of the wild type albumin and/or FLt3L polypeptides. Desirably, the additional amino acids do not interfere with the biological function of the functional portion.

Included in the scope of the invention are functional variants of the inventive polypeptides, and proteins described herein. The term "functional variant" as used herein refers to either the albumin and/or Flt3L polypeptide, or fusion protein having substantial or significant sequence identity or similarity to the albumin and/or Flt3L polypeptide, or fusion protein, which functional variant retains the biological activity of the albumin and/or Flt3L polypeptide, or fusion protein of which it is a variant. In reference to the original albumin and/or Flt3L polypeptide, or protein, the functional variant can, for instance, be at least about 30%, 50%, 75%, 80%, 90%, 98% or more identical in amino acid sequence to the albumin and/or Flt3L polypeptide, or protein.

The functional variant can, for example, comprise the amino acid sequence of the albumin and/or Flt3L polypeptide fusion protein with at least one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Functional variants can also include extensions of the albumin and/or Flt3L polypeptide fusion protein. For example, a functional variant of the albumin and/or Flt3L polypeptide fusion protein can include 1, 2, 3, 4 and 5 additional amino acids from either the N-terminal or C-terminal end of the albumin and/or Flt3L polypeptide fusion protein.

Alternatively or additionally, the functional variants can comprise the amino acid sequence of the albumin and Flt3L polypeptide fusion protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the albumin and Flt3L polypeptide fusion protein.

The albumin and Flt3L polypeptide fusion protein can consist essentially of the specified amino acid sequence or sequences described herein, such that other components of the functional variant, e.g., other amino acids, do not materially change the biological activity of the functional variant.

It will be understood by those of ordinary skill in the art that the orientation of the two proteins in the fusion protein construct can be reversed, i.e., the N-terminal protein can comprise the Flt3L ligand protein and the C-terminal protein can comprise the albumin protein.

In accordance with one or more embodiments, the albumin protein can be conjugated to the Flt3L ligand protein through the use of a chemical linker. The linker can be an ester bond, amide bond, carbonate bond, hydrozone, or any amino acid with a side chain having a free amino, carboxyl or thiol group, or a short peptide or amino acid linker.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-a-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |

TABLE 1-continued

Non-natural Amino Acids

| Non-conventional amino acid | Code | Non-conventional amino acid | Code |
|---|---|---|---|
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

In some embodiments, the Flt3L protein in the fusion protein is mammalian. In certain embodiments, the Flt3L protein can be murine, porcine, ovine, bovine, human, or combinations thereof.

In accordance with an embodiment, the present invention provides a composition comprising a polypeptide encoding human albumin protein, or a functional portion or fragment, or variant thereof, linked to a polypeptide encoding human Flt3L protein, or a functional portion or fragment, or variant thereof, such as, for example, SEQ ID NO: 1.

In accordance with an embodiment, the present invention provides a composition comprising a polypeptide encoding murine albumin protein, or a functional portion or fragment, or variant thereof, linked to a polypeptide encoding human Flt3L protein, or a functional portion or fragment, or variant thereof, such as, for example, SEQ ID NO: 2.

In accordance with an embodiment, the present invention provides a composition comprising a polypeptide encoding murine albumin protein, or a functional portion or fragment, or variant thereof, linked to a polypeptide encoding murine Flt3L protein, or a functional portion or fragment, or variant thereof, such as, for example, SEQ ID NO: 3.

In accordance with an embodiment, the present invention provides a composition comprising a polypeptide encoding human albumin protein, or a functional portion or fragment, or variant thereof, linked to a polypeptide encoding murine Flt3L protein, or a functional portion or fragment, or variant thereof.

In accordance with an embodiment, the present invention provides a method of treating a tumor cell comprising administering to the cell an effective amount of a composition comprising a polypeptide encoding albumin protein, or a functional portion or fragment, or variant thereof linked to a polypeptide encoding Flt3L protein, or a functional portion or fragment, or variant thereof.

In accordance with an embodiment, the present invention provides a method of treating a tumor cell comprising administering to the cell an effective amount of a composition comprising a polypeptide encoding albumin protein, or a functional portion or fragment, or variant thereof linked to a polypeptide encoding Flt3L protein, or a functional portion or fragment, or variant thereof, in combination either simultaneously or serially with at least one other chemotherapeutic or radiation treatment.

In accordance with an embodiment, the present invention provides a method of treating cancer in a subject in need thereof, comprising administering to the subject an effective amount of a composition comprising a polypeptide encoding albumin protein, or a functional portion or fragment, or variant thereof linked to a polypeptide encoding Flt3L protein, or a functional portion or fragment, or variant thereof.

In accordance with some embodiments, the present invention provides fusion protein compositions comprising the polypeptide molecules described herein, and a pharmaceutically acceptable carrier.

In accordance with an embodiment, the present invention provides a use of a composition comprising a polypeptide encoding albumin protein, or a functional portion or fragment, or variant thereof linked to a polypeptide encoding Flt3L protein, or a functional portion or fragment, or variant thereof, in an amount effective for use in a medicament, and most preferably for use as a medicament for treating a disease or disorder associated with a neoplastic disease in a subject. In a preferred embodiment, the neoplastic disease is associated with a solid tumor, a hematological tumor, or wherein the tumor and/or its micro and macrometastases is selected from the group consisting of breast cancer, prostate cancer, pancreatic cancer, colon cancer, hepatoma, glioblastoma, ovarian cancer, leukemia, Hodgkin's lymphoma and multiple myeloma.

In accordance with another embodiment, the term "cancer" includes cancers in tissues that can tolerate high doses of radiation. A high dose of radiation would include doses greater than 2 Gy.

In yet another embodiment, the cancers treated by the present invention would also include cancers which are resistant to hypoxia, chemotherapy, such as, for example, tamoxifen or taxol resistant cancers, and cancers already resistant to radiation therapy.

In accordance with another embodiment, the present invention provides a method of treating cancer in a subject comprising a) administering to the subject an effective amount of a pharmaceutical composition comprising a fusion polypeptide encoding albumin protein, or a functional portion or fragment, or variant thereof linked to a polypeptide encoding Flt3L protein, or a functional portion or fragment, or variant thereof, and a pharmaceutically acceptable carrier, in one or more doses, and b) administering ionizing radiation to the subject in proximity to the location of the cancer in the subject.

In an embodiment, the term "administering" means that the compounds of the present invention are introduced into a subject, preferably a subject receiving treatment for cancer, and the compounds are allowed to come in contact with the one or more disease related cells or population of cells in vivo.

As used herein, the term "treatment," as well as words stemming therefrom, includes diagnostic and preventative as well as disorder remitative treatment, including, but not limited to administering one or more doses of radiotherapy to a subject or a cell or population of cells, including the use of focused radiation such as stereotactic ablative radiotherapy (SABR), stereotactic radiosurgery (SRS) and stereotactic body radiation therapy (SBRT) methods. It will be understood that a subject may undergo more than one treatment or cycle of radiotherapy to be effective in reducing tumor volume or initiate cancer/target cell death.

Radiation therapy, radio-immunotherapy or pre-targeted radioimmunotherapy are used for the treatment of diseases of oncological nature. "Radiotherapy", or radiation therapy, means the treatment of cancer and other diseases with ionizing radiation. Ionizing radiation deposits energy that injures or destroys cells in the area being treated (the target tissue) by damaging their genetic material, making it impossible for these cells to continue to grow. Radiotherapy may be used to treat localized solid tumors, such as cancers of the skin, tongue, larynx, brain, breast, lung or uterine cervix. It can also be used to treat leukemia and lymphoma, i.e. cancers of the blood-forming cells and lymphatic system, respectively. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy. Gamma rays are another form of photons used in radiotherapy. Gamma rays are produced spontaneously as certain elements (such as radium, uranium, and cobalt 60) release radiation as they decompose, or decay. Another technique for delivering radiation to cancer cells is to place radioactive implants directly in a tumor or body cavity. This is called internal radiotherapy. Brachytherapy, interstitial irradiation, and intracavitary irradiation are types of internal radiotherapy. In this treatment, the radiation dose is concentrated in a small area, and the patient stays in the hospital for a few days. Internal radiotherapy is frequently used for cancers of the tongue, uterus, and cervix. A further technique is intra-operative irradiation, in which a large dose of external radiation is directed at the tumor and surrounding tissue during surgery. Another approach is particle beam radiation therapy. This type of therapy differs from photon radiotherapy in that it involves the use of fast-moving subatomic particles to treat localized cancers. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation. Radio-sensitizers make the tumor cells more likely to be damaged, and radio-protectors protect normal tissues from the effects of radiation.

As used herein, the term "subject" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It will be understood to those of skill in the art that the term "therapeutic agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications. In preferred embodiments, the disease is a neoplastic disease such as cancer.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a neoplastic or proliferative disease such as a tumor or cancer. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with an embodiment, the present invention provides a method of treating cancer in a subject in need thereof, comprising administering to the subject an effective amount of a composition comprising a fusion polypeptide encoding albumin protein linked to a polypeptide encoding Flt3L protein and an effective amount of at least one PD-1 inhibiting agent or other checkpoint inhibitor.

In accordance with one or more embodiments, the present invention provides methods of treatment of tumors using focused radiation on a subject to initiate an immune response in the subject, followed by administration of a composition comprising a fusion polypeptide encoding albumin protein linked to a polypeptide encoding Flt3L protein and an immunotherapeutic agent, such as a PD-1 antibody, to bypass immune checkpoints and sustain the immune response in the subject.

Therefore, in accordance with an embodiment, the present invention provides methods for treating a tumor in a subject in need of treatment thereof, the method comprising administering to the subject a therapeutically effective dose of focused radiation to treat the tumor in combination with a composition comprising a fusion polypeptide encoding albumin protein linked to a polypeptide encoding Flt3L protein, at least one immunotherapeutic agent comprising an immune checkpoint inhibitor, and at least one chemotherapeutic agent.

As used herein, the term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

It will be understood by those of ordinary skill in the art, that the term "immune checkpoints" means a group of molecules on the cell surface of CD4 and CD8 T cells. These molecules effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. immunotherapeutic agents which can act as immune checkpoint inhibitors useful in the methods of the present invention, include, but are not limited to, anti-B7-H4; anti-PD1 or anti-B7-H1; anti-CTLA-4 (ipilimumab) and anti-LAG3.

More particularly, as also described in more detail herein below, ipilimumab (anti-CTLA-4) is a fully human, antagonistic monoclonal antibody that binds to CTLA-4. CTLA-4 is a cell-surface protein expressed on certain CD4 and CD8 T cells; when engaged by its ligands (B7-1 and B7-2) on APCs, T-cell activation and effector function are inhibited. When an antibody to CTLA-4 is administered, the CTLA-4 receptor can no longer bind to these ligands, and T-cell responses are unrestrained. Ipilimumab has been evaluated in a number of clinical trials in melanoma, renal cell cancer, and more recently in prostate cancer.

In accordance with another embodiment of the present invention, another immune checkpoint that could potentially be exploited for treating certain cancers is the inhibitory co-receptor known as programmed death 1 (PD-1 or CD279). Among the CD8 T cells that infiltrate the prostate gland in men with cancer, up to 87% express PD-1. Tumor-specific expression of the major ligand of PD-1, B7-H1, is associated with poor prognosis in kidney cancer, as well as in other cancers in humans. Conversely, in multiple systems blocking PD-1: B7-H1 interactions causes tumors to regress. MDX-1106 is a genetically engineered, fully human immunoglobulin G4 (IgG4) monoclonal antibody specific for human PD-1 that was recently evaluated in a phase 1, dose-escalation trial.

In accordance with alternative embodiments of the present invention, immunotherapeutic agents can include proteins and/or antibodies to proteins and biomolecules including, for example, B- and T-lymphocyte attenuator protein (BTLA), Tim3, CD160, KIR antagonist antibodies, 4-1BB, OX40, CD27 and CD4.

Without wishing to be bound to any one particular theory, it is thought that focused radiation effectively disrupts the tumor microenvironment and causes presentation of tumor antigens to effectively act as a vaccine-like response. Current cancer vaccines are limited by the lack of tumor specific antigens. One advantage of focused radiation as compared to vaccines is that focused radiation precisely targets the tumor alone to cause spillage of multiple antigens that would be specific to the tumor.

As used herein the term "tumor microenvironment" includes the cells, including normal cells, molecules, and blood vessels that surround and feed a tumor cell. A tumor can change its microenvironment, and the microenvironment can affect how a tumor grows and spreads. More particularly, the tumor microenvironment is a complex system of many cells, which all can participate in tumor progression, including endothelial cells and their precursors, pericytes, smooth-muscle cells, fibroblasts of various phenotypes, myofibroblasts, neutrophils and other granulocytes (eosinophils and basophils), mast cells, T, B and natural killer lymphocytes, and antigen-presenting cells, such as macrophages and dendritic cells. The components of the microenvironment generally can be grouped into four categories: cancer cells, non-cancer cells, secreted soluble factors, and non-cellular solid material, including the extracellular matrix.

As described in more detail herein below, the focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray).

In accordance with one or more embodiments, the present invention provides methods for administering a therapeutically effective amount of a composition comprising a fusion polypeptide encoding albumin protein linked to a polypeptide encoding Flt3L protein in combination with the therapeutically effective dose of focused radiation.

In particular embodiments, the other immunotherapeutic agents are selected from the group consisting of monoclonal antibodies, immune effector cells, vaccines, including dendritic cell vaccines, and cytokines.

As described in further detail herein below, the monoclonal antibodies used in the inventive compositions and methods can be selected from the group consisting of anti-PD-1 antibody, alemtuzumab, bevacizumab, brentuximab vedotin, cetuximab, gemtuzumab ozogamicin, ibritumomab tiuxetan, ipilimumab (anti-CTLA-4), ofatumumab, panitumumab, rituximab, tositumomab, trastuzumab, anti-B7-H4, anti-B7-H1, anti-LAG3, BTLA, anti-Tim3, anti-B7-DC, anti-CD160, KIR antagonist antibodies, anti-4-1BB, anti-OX40, anti-CD27, and CD40 agonist antibodies.

In accordance with a further embodiment, the present invention provides a pharmaceutical composition comprising a fusion polypeptide encoding albumin protein linked to a polypeptide encoding Flt3L protein, wherein the composition includes a pharmaceutically and physiologically acceptable carrier, in an amount effective for use in a medicament, and most preferably for use as a medicament for inducing an immune response, or treating cancer, or inhibiting the growth of a tumor, or neoplasm in a subject who receives or will receive focused radiation treatment, when administered to the subject in an effective amount.

In accordance with a further embodiment, the present invention provides a pharmaceutical composition comprising a polypeptide encoding albumin protein linked to a fusion polypeptide encoding Flt3L protein, and at least one immunotherapeutic agent, wherein the composition includes a pharmaceutically and physiologically acceptable carrier, in an amount effective for use in a medicament, and most preferably for use as a medicament for inducing an immune response, or treating cancer, or inhibiting the growth of a tumor, or neoplasm in a subject who receives or will receive focused radiation treatment, when administered to the subject in an effective amount.

In accordance with yet another embodiment, the present invention provides a neoadjuvant strategy or treatment regimen for treating cancer. It will be understood by those of ordinary skill in the art, that the term "neoadjuvant therapy" includes the administration of a polypeptide encoding albumin protein linked to a fusion polypeptide encoding Flt3L protein with or without the addition of one or more therapeutic or immunotherapeutic agents in combination with focused radiation before, or in conjunction with, traditional chemotherapy/radiation treatment and adjuvant therapy. Neoadjuvant therapy aims to reduce the size or extent of the cancer before using radical treatment intervention, thus making procedures easier and more likely to succeed, and reducing the consequences of a more extensive treatment technique that would be required if the tumor wasn't reduced in size or extent.

For example, in one non-limiting strategy, a patient is administered focused radiation in combination with a first dose of the fusion protein possibly followed by an antibody days after receiving a result from a biopsy. After a period of time later, for example, a week later, the patient can undergo surgery. Following surgery, for example, two weeks after surgery, the patient is administered focused radiation in combination with a second dose of the fusion protein possibly followed by an antibody. After another period of time, for example two weeks later, the patient is administered focused radiation in combination with a third dose of the fusion protein possibly followed by an antibody. One of ordinary skill in the art would recognize upon review of the presently disclosed subject matter that the treatment regimen presented herein can be adjusted or modified to meet the therapeutic needs of an individual patient. For example, any of the steps disclosed herein can be repeated in series, or individually, to meet such needs.

In accordance with another embodiment, the present inventive methods further comprise administering to the subject additional chemotherapy, immunotherapy and or radiation treatment. In other embodiments, the method further comprises administering to the subject, adjuvant therapy.

In accordance with another embodiment, the present inventive methods further comprise administering at least one adjuvant to the subject in combination with a fusion polypeptide encoding albumin protein linked to a polypeptide encoding Flt3L protein with, or without the at least one immunotherapeutic agent and/or immune checkpoint inhibitor. In particular embodiments, the adjuvant is selected from the group consisting of a cytokine, an interleukin, an interferon, a granulocyte-macrophage colony-stimulating factor (GM-CSF), Bacille Clamette-Guérin (BCG), a keyhole limpet memocyanin (KLH), incomplete Freund's adjuvant (IFA), QS-21, DETOX, and dinitrophenyl.

It will be understood that the inventive methods can be used to treat many tumors, both benign and malignant. In one or more embodiments, the invention provides methods and compositions for treating cancers, including, for example, cancers which exist as solid tumors in a subject. One of ordinary skill in the art, upon review of the presently disclosed subject matter, would understand that other tumors, including solid tumors, lesions, and conditions can be treated by the presently disclosed methods including, but not limited to, cancers involving the cervix, ovaries, head and neck, brain; cancers involving the spine; lung cancers; pancreatic cancers; prostate cancers; liver cancers, kidney cancers; breast cancers, melanoma, metastatic orbital tumors, orbital lymphomas, and orbital inflammations.

In general, the "effective amount" of an agent, e.g., the fusion protein compositions, a dose of radiation and/or an immunotherapeutic agent, refers to the amount necessary to elicit the desired biological response. As will be appreciated by those of ordinary skill in this art, the effective amount of an agent may vary depending on such factors as the desired biological endpoint, the agent to be delivered, the makeup of the agent, the target tissue, and the like.

The term "combination" is used in its broadest sense and means that a subject is administered at least two agents, e.g., a dose of radiation and at least a fusion polypeptide encoding albumin protein linked to a polypeptide encoding Flt3L protein, with, or without at least one additional immunotherapeutic agent, e.g., monoclonal antibodies, immune effector cells, vaccines, including dendritic cell vaccines, and cytokines, as described herein or as otherwise known in the art.

In accordance with one or more embodiments of the methods of the present invention, the timing of administration of a dose of radiation and at least a fusion polypeptide encoding albumin protein linked to a polypeptide encoding Flt3L protein, with, or without at least one additional immunotherapeutic agent, can be varied so long as the beneficial effects of the combination of these agents are achieved. Accordingly, the phrase "in combination with" refers to the administration of a dose of radiation and at least one immunotherapeutic agent either simultaneously, sequentially, or a combination thereof. Therefore, a subject administered a combination of a dose of radiation and at least a fusion polypeptide encoding albumin protein linked to a polypeptide encoding Flt3L protein, with, or without at least one additional immunotherapeutic agent can receive a dose of radiation and at least one immunotherapeutic agent at the same time (i.e., simultaneously) or at different times (i.e., sequentially, in either order, on the same day or on different days), so long as the effect of the combination of both agents is achieved in the subject.

It will be understood by those of ordinary skill, that when administered sequentially, a fusion polypeptide encoding albumin protein linked to a polypeptide encoding Flt3L protein, with, or without at least one additional immunotherapeutic agent, can be administered within 1, 5, 10, 30, 60, 120, 180, 240 minutes or longer of one another. In other embodiments, agents administered sequentially, can be administered within 1, 5, 10, 15, 20 or more days of one another. When more than one therapeutic agent is administered in combination with a dose of radiation, and the agents are administered either sequentially or simultaneously, they can be administered to the subject as separate pharmaceutical compositions, each comprising either one therapeutic agent and at least one immunotherapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent(s) was administered as a single agent. The effects of multiple agents may, but need not be, additive or synergistic. The agents may be administered multiple times.

As used herein, the terms "synergy," "synergistic," "synergistically" and derivations thereof, such as in a "synergistic effect" or a "synergistic combination" or a "synergistic composition" refer to circumstances under which the biological activity of a combination of a dose of radiation and at least one additional therapeutic agent is greater than the sum of the biological activities of the respective agents when administered individually.

Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

Focused radiation methods suitable for use with the presently disclosed methods include, but are not limited to, stereotactic radiosurgery, fractionated stereotactic radiosurgery, and intensity-modulated radiation therapy (IMRT).

Because of noninvasive fixation devices, stereotactic radiation need not be delivered in a single treatment. The treatment plan can be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment.

In an embodiment, the dosage of radiation applied using stereotactic radiosurgery can vary. In some embodiments, the dosage can range from 1 Gy to about 30 Gy, and can encompass intermediate ranges including, for example, from 1 to 5, 10, 15, 20, 25, up to 30 Gy in dose.

The main advantage of fractionation is that it allows higher doses to be delivered to tumorous tissue because of an increased tolerance of the surrounding normal tissue to these smaller fractionated doses. Accordingly, while single-dose stereotactic radiation takes advantage of the pattern of radiation given, fractionated stereotactic radiation takes advantage of not only the pattern of radiation, but also of the differing radiosensitivities of normal and surrounding tumorous tissues. Another advantage of fractionated stereotactic radiation is so-called "iterative" treatment, in which the shape and intensity of the treatment plan can be modified during the course of therapy.

Fractionated stereotactic radiosurgery can result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation can kill more normal tissue than several smaller doses of radiation can. Accordingly, multiple smaller doses of radiation can kill more tumor cells while sparing normal tissue.

In an embodiment, the dosage of radiation applied using fractionated stereotactic radiation can vary. In some embodiments, the dosage can range from 1 Gy to about 50 Gy, and can encompass intermediate ranges including, for example, from 1 to 5, 10, 15, 20, 25, 30, 40, up to 50 Gy in hypofractionated doses.

It will be understood by those of ordinary skill in the art that stereotactic radiosurgery can be characterized by the source of radiation used, including particle beam (proton), cobalt-60 (photon-Gamma Knife®), and linear accelerator (x-ray). A linear accelerator produces high-energy X-ray radiation and is capable of delivering precise and accurate doses of radiation required for radiosurgery. Radiosurgery using a linear accelerator is typically carried out in multi-session, smaller dose treatments so that healthy surrounding tissue is not damaged from too high a dose of radiation. Radiosurgery using linear accelerator technology also is able to target larger brain and body cancers with less damage to healthy tissues. The most common uses of linear accelerator stereotactic radiosurgery are for the treatment of metastatic cancer, some benign tumors and some arterio-venous malformations. Linear accelerator based machines are not dedicated to treatments only within the brain and can be used throughout the body, as well as the head and neck.

As used with the inventive methods and compositions provided herein, a "gamma knife" uses multiple, e.g., 192 or 201, highly-focused x-ray beams to make up the "knife" that cuts through diseased tissue. The gamma knife uses precisely targeted beams of radiation that converge on a single point to painlessly "cut" through brain tumors, blood vessel malformations, and other brain abnormalities. A gamma knife makes it possible to reach the deepest recesses of the brain and correct disorders not treatable with conventional surgery.

In accordance with the inventive methods and compositions, use of proton beam radiation offers certain theoretical advantages over other modalities of stereotactic radiosurgery (e.g., Gamma Knife® and linear accelerators), because it makes use of the quantum wave properties of protons to reduce doses of radiation to surrounding tissue beyond the target tissue. In practice, the proton beam radiation offers advantages for treating unusually shaped brain tumors and arteriovenous malformations. The homogeneous doses of radiation delivered by a proton beam source also make fractionated therapy possible. Proton beam radiosurgery also has the ability to treat tumors outside of the cranial cavity. These properties make proton beam radiosurgery efficacious for post-resection therapy for many chordomas and certain chondrosarchomas of the spine and skull base, as well as a mode of therapy for many other types of tumors.

In accordance with another embodiment of the inventive methods and compositions, intensity-modulated radiation therapy (IMRT) can be used. IMRT is an advanced mode of high-precision three-dimensional conformal radiation therapy (3DCRT), which uses computer-controlled linear accelerators to deliver precise radiation doses to a malignant tumor or specific areas within the tumor. In 3DCRT, the profile of each radiation beam is shaped to fit the profile of the target from a beam's eye view (BEV) using a multileaf collimator (MLC), thereby producing a number of beams. More particularly, IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel.

Treatment with IMRT is planned by using 3-D computed tomography (CT) or magnetic resonance (MRI) images of the patient in conjunction with computerized dose calculations to determine the dose intensity pattern that will best conform to the tumor shape. Typically, combinations of multiple intensity-modulated fields coming from different beam directions produce a custom tailored radiation dose that maximizes tumor dose while also minimizing the dose to adjacent normal tissues. Because the ratio of normal tissue dose to tumor dose is reduced to a minimum with the IMRT approach, higher and more effective radiation doses can safely be delivered to tumors with fewer side effects compared with conventional radiotherapy techniques. IMRT typically is used to treat cancers of the prostate, head and neck, and central nervous system. IMRT also has been used to treat breast, thyroid, lung, as well as in gastrointestinal, gynecologic malignancies and certain types of sarcomas.

Cancer vaccines have been studied for several decades, but advances in this field have been slower than for other forms of immunotherapy and they are still mostly experimental treatments at this time. Vaccines, in general, use weakened or killed viruses, bacteria, or other germs to trigger an immune response in the body to defend against a foreign antigen. Cancer vaccines are designed to work the same way. For example, new vaccines against the human papilloma virus (HPV) help prevent cervical, vaginal, vulvar, and anal cancer. Vaccines against hepatitis B virus (HBV) may lower some subject's risk of getting liver cancer. But these vaccines don't target cancer cells; they target the viruses that can cause these cancers.

True cancer vaccines are different from the vaccines that work against viruses. Instead of preventing disease, they are meant to promote the immune system to attack the cancer itself. A true cancer vaccine has cancer cells, parts of cells, or pure antigens. The vaccine increases the immune response against cancer cells that are already in the body and can be combined with other substances or cells called adjuvants that help boost the immune response.

Cancer vaccines are characterized as active immunotherapies because they are meant to trigger a subject's own immune system to respond. Further, cancer vaccines are specific because they should only affect cancer cells. Such vaccines don't just boost the immune system in general; they cause the immune system to attack cancer cells with one or more specific antigens. At this time, only one true cancer vaccine has been approved by the FDA. Sipuleucel-T (Provenge®) is used to treat advanced prostate cancer. In this vaccine, white blood cells (cells of the immune system) are removed from the patient's blood and exposed to a protein from prostate cancer cells called prostatic acid phosphatase (PAP). These exposed cells are then given back to the patient by infusion into a vein (IV). Once in the body, the cells make other immune system cells attack the patient's prostate cancer.

Other types of cancer vaccines are currently being studied including, but not limited to, tumor cell vaccines, including autologous and allogeneic tumor cell vaccines; antigen vaccines, which boost the immune system by using only one or a few antigens, e.g., proteins or peptides; dendritic cell vaccine, which include special antigen-presenting cells (APCs) that help the immune system recognize cancer cells by breaking down cancer cells into smaller pieces (including antigens), then present these antigens to T cells making it easier for the immune system cells to recognize and attack them; anti-idiotype vaccines, which show promise as a B-cell lymphoma; DNA vaccines, and vector-based vaccines, which use special delivery systems (called vectors) to make them more effective and can include, for example, vector-based antigen vaccines and vector-based DNA vaccines.

The types of cancers for which tumor cell vaccines can be used in conjunction with the inventive fusion proteins include, but are not limited to, melanoma, kidney cancer, ovarian cancer, breast cancer, colorectal cancer, lung cancer, prostate cancer, non-Hodgkin lymphoma, and leukemia. Antigen vaccines are being studied to be used against these cancers, among others: breast cancer, prostate cancer, colorectal cancer, ovarian cancer, melanoma, kidney cancer, pancreatic cancer, and multiple myeloma. The dendritic cell vaccine approach is being studied for use in subjects with these and other cancers: prostate cancer, melanoma, kidney cancer, colorectal cancer, lung cancer, breast cancer, leukemia, and non-Hodgkin lymphoma. Sipuleucel-T (Provenge), which is approved to treat advanced prostate cancer, is an example of a dendritic cell vaccine. DNA vaccines are now being studied in clinical trials for use against the following cancers, among others: melanoma, leukemia, prostate cancer, and head and neck cancers.

The precise effective amount of the inventive fusion peptide compositions for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

With respect to the inventive fusion peptide compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compositions comprising the fusion proteins, polypeptides or functional fragments thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular peptide containing compositions, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as a neoplastic disease or tumor.

It is also contemplated that in an embodiment of the present invention, the methods of treatment disclosed herein are useful against many mammalian tumors, including, for example, cervical cancer, breast cancer, prostate cancer, pancreatic cancer, colon cancer, hepatoma, glioblastoma, ovarian cancer, and head and neck cancers.

It will be understood by those of ordinary skill in the art that the term "tumor" as used herein means a neoplastic growth which may, or may not be malignant. Additionally, the compositions and methods provided herein are not only useful in the treatment of tumors, but in their micrometastses and their macrometastses. Typically, micrometastasis is a form of metastasis (the spread of a cancer from its original location to other sites in the body) in which the newly formed tumors are identified only by histologic examination; micrometastases are detectable by neither physical exam nor imaging techniques. In contrast, macrometastses are usually large secondary tumors.

In accordance with an embodiment, the present invention provides compositions and methods for the prevention and/or treatment of tumors, and their micrometastses and their macrometastses.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Mice. Five- to seven-week old female C57BL/6 mice were purchased from Charles River Laboratories (Frederick, MD). All animal procedures and injections were performed using approved protocols by the Johns Hopkins Institutional Animal Care and Committee. Recommendations for the proper use and care of laboratory animals were closely followed.

BMDC culture. Bone marrow derived dendritic cells were grown using previously described methods (13). Briefly, C57BL/6 mice were euthanized in accordance with Johns Hopkins approved animal use protocols. Femurs were collected and bone marrow cells were eluted using a 26G needle with syringe and complete RPMI (RPMI 1640 supplemented with 10% fetal bovine serum, 50 units/ml of penicillin/streptomycin, 2 mM L-glutamine, 1 mM sodium pyruvate, and 2 mM non-essential amino acids). After elution, cells were 70 μm filtered. Cells were then RBC lysed using RBC lysis buffer (Santa Cruz Biotechnology, Dallas, TX). Following extensive washing in complete RPMI, cells were plated at $2 \times 10^6$ cells in 2 ml complete RPMI supplemented with either GM-CSF 20 ng/ml (Genescript, Piscataway, NJ), human-Flt3L 100 ng/ml (Genescript, Piscataway, NJ), or Alb-Flt3L 500 ng/ml in a 6 well plate. 3 days following initial setup, 2 ml of respective cytokine supplemented media was added to each well. On day 7, cells were harvested using 5 μM EDTA/PBS and prepared for flow cytometric analysis.

Preparation of single cell suspensions from whole blood or draining lymph nodes. Whole blood was collected from mice into EDTA coated tubes and subsequently RBC lysed using RBC lysis buffer (Santa Cruz Biotechnology, Dallas, TX). Following this, samples were 70 μm filtered, washed in PBS, and then prepared for flow cytometric analysis.

Alternatively, draining lymph nodes (inguinal and auxiliary) were collected into complete media (prepared as previously described). Lymph nodes were ground and 70 μm filtered. Cells were then RBC lysed, washed with PBS, and reserved for flow cytometry.

Flow cytometry for extracellular markers and CD8+ T cell E7 tetramer staining. Following preparation of single cell suspension, cells were moved to 96 well V-bottom plates and stained for flow cytometric analysis. Briefly, cells were washed with FACS buffer (0.1% BSA/PBS) and then live/dead stained using Zombie Aqua in PBS (Biolegend San Diego, CA). Cells were then washed with FACS buffer and Fc blocked using anti-mouse CD16/32 (Biolegend San Diego, CA). Following this, cells were stained with the appropriate anti-mouse antibodies: Brilliant Violet 421 (BV) CD11c (Clone: N418), Phycoerythrin/Cyanine7 (PE/Cy) I-A/I-E (Clone: M5/114.15.2), Alexa Fluor 488 CD45R/B220 (Clone: RA3-6B2), Allophycocyanin (APC) Siglec H (Clone: 551), APC/Fire 750 CD8a (Clone: 53-6.7), PerCP/Cy5.5 CD19 (Clone: 1D3), Alexa Fluor 488 GR-1 (Clone: RB6-8C5), BV785 CD4 (Clone: RM4-5), PE/Cy7 CD3 (Clone: 17A2). Antibodies, as well as appropriate isotype controls were purchased from either Biolegend (San Diego, CA), or eBioscience/Thermo Fisher (Waltham, MA) and titrated to a suitable concentration. For CD8+ T cell E7 specific tetramer staining, cells were stained with PE conjugated HPV16 H2-KD-RAHYNIVTF tetramer alongside other appropriate fluorescently conjugated antibodies.

Intracellular cytokine staining for flow cytometric analysis. The cells were harvested as previously described, and were resuspended in complete RPMI containing Brefeldin A (5 μg/ml), Monensin (2 μM), PMA (20 ng/ml), and ionomycin (1 μg/ml) for 4 hours. Cells were then washed and stained for extracellular markers as described. Following extracellular staining, cells were fixed/permeabilized using ebioscience FoxP3 transcription factor kit (catalog #5523, ebioscience/Thermo Fisher, Waltham, MA) according to kit instructions. Appropriate intracellular cytokines or transcription factors were stain for using anti-mouse antibodies including: Alexa Fluor 488 Ki-67 (Clone: 16A8), and APC IFNg (Clone: XMG1.2). Antibodies, as well as appropriate isotype controls and reagents were purchased from Biolegend (San Diego, CA).

Acquisition and analysis of flow cytometric samples. Flow samples were acquired on a Beckman Coulter CytoFLEX S using CytExpert 2.0 software (Beckman Coulter, Brea, CA). Auto compensation for multiparameter analysis was done using included compensation software in CytExpert 2.0 using appropriate isotype, fluorescence minus one, and single staining controls. For dendritic cell analysis, 50,000 live cells were acquired, and for T cell analysis, 50000 CD8+ T cells were acquired. Analysis was done using CytExpert 2.0 or FlowJo version 10 (Treestar, Ashland, OR).

Statistical Analysis.

All statistical analysis were completed using Graph Pad Prism 5 (La Jolla, CA). Data presented in this application are expressed as mean±SEM. Data points were compared using student's t-test. Survival curve was generated using Kaplan-Meier survival curve and compared using logrank test. p values<0.05 were considered significant.

OVA immunizations in combination with Alb-Flt3L.

Mice were injected with Flt3L or Alb-Flt3L. Fresh OVA protein (Sigma Aldrich, St. Louis, MO) was dissolved in PBS and 0.2 μm filtered prior to injection. On day 20 after initial injection, blood was collected in EDTA coated tubes. Samples were centrifuged and serum was collected and saved for ELISA. Remaining cells were RBC lysed and stain for flow cytometric analysis as described.

For analysis of OVA specific antibody titers, high-binding ELISA plates (Genesee scientific, San Diego, CA) were coated overnight with 2 μg/ml OVA protein in 0.1M Sodium carbonate/bicarbonate buffer pH to 9.5. The following day, cells were washed using 0.05% Tween-20/PBS and blocked with 10% FBS/PBS. Serum samples were diluted from $1:10^1$-$1:10^8$ and added to ELISA plates in triplicate. Signal was detected using biotinylated antimouse IgG1 (Clone: RMG1-1) or IgG2a (Clone: RMG2a-62) and subsequent streptavidin-HRP. TMB substrate (Catalog #555214) was used to develop signal and absorbance was measured using dual measurement at 450 nm and 570 nm on an xMark plate spectrophotometer (Bio-Rad, Hercules, CA). Positive titer was set as two standard deviations above absorbance for naïve mice at a given titer.

Fluorescently labeled cytokines were generated by labeling 1 mg of Flt3L or Alb-Flt3L with Alexa Fluor 647 NHS ester primary amine labeling kit (Invitrogen/Thermo Fisher, Waltham, MA) according to kit instructions. Following labeling, products were purified using extensive dialysis for 24 hours. Fluorescent cytokines were then injected s.c. into C57BL/6 mice. 16 hours later, mice were euthanized and tissues harvested. Subsequent imaging was performed on an IVIS spectrum in vivo imaging system (Perkin Elmer, Waltham, MA). Following IVIS imaging, draining lymph nodes (inguinal and auxiliary) were ground and single cell suspensions acquired as previously described. Cells were then stained as described and analyzed by flow cytometry.

Plasmid DNA constructs and Alb-Flt3L protein preparations.

All data shown utilized mouse albumin-human Flt3L (Alb-Flt3L). This construct, as well as mouse albumin-mouse Flt3L and human albumin-human Flt3L have been generated using the following methods. For the generation of pcDNA3-Malb (mouse albumin), Malb was first amplified with PCR using cDNA template of mouse albumin (AAH49971) purchased from transOMIC technologies (Huntsville, AL) and a set of primers, 5'-AAATCTAGAGC-CACCATGAAGTGGGTAACCTTT-3' (SEQ ID NO: 4) and 5'-TTTGAATTCGGCTAAGGCGTCTTTGCATC-3' (SEQ ID NO: 5). The amplified product was then cloned into the XbaI/EcoRI sites of pcDNA3 vector (Invitrogen Corp., Carlsbad, California, USA).

Next, for generation of pcDNA3-Halb (human albumin), Halb was first amplified with PCR using cDNA template of human albumin (NM_000477) purchased from transOMIC technologies (Huntsville, AL) and a set of primers, 5'-AAACTCGAGGCCACCATGAAGTGGGTAACCTTT-3' (SEQ ID NO: 6) and 5'-TTTGAATTCTAAGCCTAA-GGCAGCTTGAC-3' (SEQ ID NO: 7). The amplified product was then cloned into the XbaI/EcoRI sites of pcDNA3 vector.

Next, for the generation of pcDNA3-HalbHflt3L, human Flt3 ligand was first PCR amplified cDNA template of human Flt3 ligand (AAA90950.1) gene synthesized from Genscript(Piscataway, NJ) and a set of primers, 5'-TTT-GAATTCGGGACACCTGACTGTTACTTC-3' (SEQ ID NO: 8) and 5'-AAACTTAAGCTACTGCCTGGGCCG-AGGCTCTGG-3' (SEQ ID NO: 9). The amplified product was then cloned into the EcoRI/Afl II sites of pcDNA3-Malb. All plasmid constructs were confirmed by DNA sequencing.

Malb, Halb, HalbHflt3L, MalbHflt3L (Alb-Flt3L) and MalbMflt3L proteins were expressed using Expi293F expression system kit (Thermo Fisher Scientific, Waltham, MA) according to manufacturer's instructions. Expi293F cells were transfected with pcDNA3-Malb, pcDNA3Halb, pcDNA3HalbHflt3L, pcDNA3MalbHflt3L and pcDNA3-MalbMflt3L, respectively. Proteins were purified by HiTrap Albumin column (GE Healthcare Life Sciences, Marlborough, MA).

Example 1

Alb-Flt3L retains biological function and generates alternative dendritic cell populations in vitro.

First, a genetic fusion protein of albumin and Flt3L was produced and purified as described above (FIGS. 1A-E). Since conjugation of any cytokine to a carrier protein can alter the cytokines function, we aimed to determine whether genetic fusion of albumin to Flt3L affected its biological function. Bone marrow derived cells were collected from C57BL/6 mice and cultured for 7 days with 20 ng/ml GM-CSF, 100 ng/ml Flt3L, or 500 ng/ml Alb-Flt3L since it is approximately 5 times the molecular weight of Flt3L. On day 7, cells were phenotyped by flow cytometry. Flt3L and Alb-Flt3L both promoted the development of dendritic cells, including total CD11c+MHCII+ cells, CD103+ DCs and CD8a+ DCs (FIGS. 2A-2D). While GM-CSF expanded CD11c+MHCII+ cells, it was unable to support the generation of either of the cross-presenting CD103+ or CD8a+ dendritic cell populations. Taken together, the data show that Alb-Flt3L retains markedly similar biological function compared to Flt3L and can skew BM cells to cross-presenting dendritic cell populations.

Example 2

Single administration of Alb-Flt3L is sufficient to generate alternative dendritic cell populations in vivo.

Figures 3A, 3B:
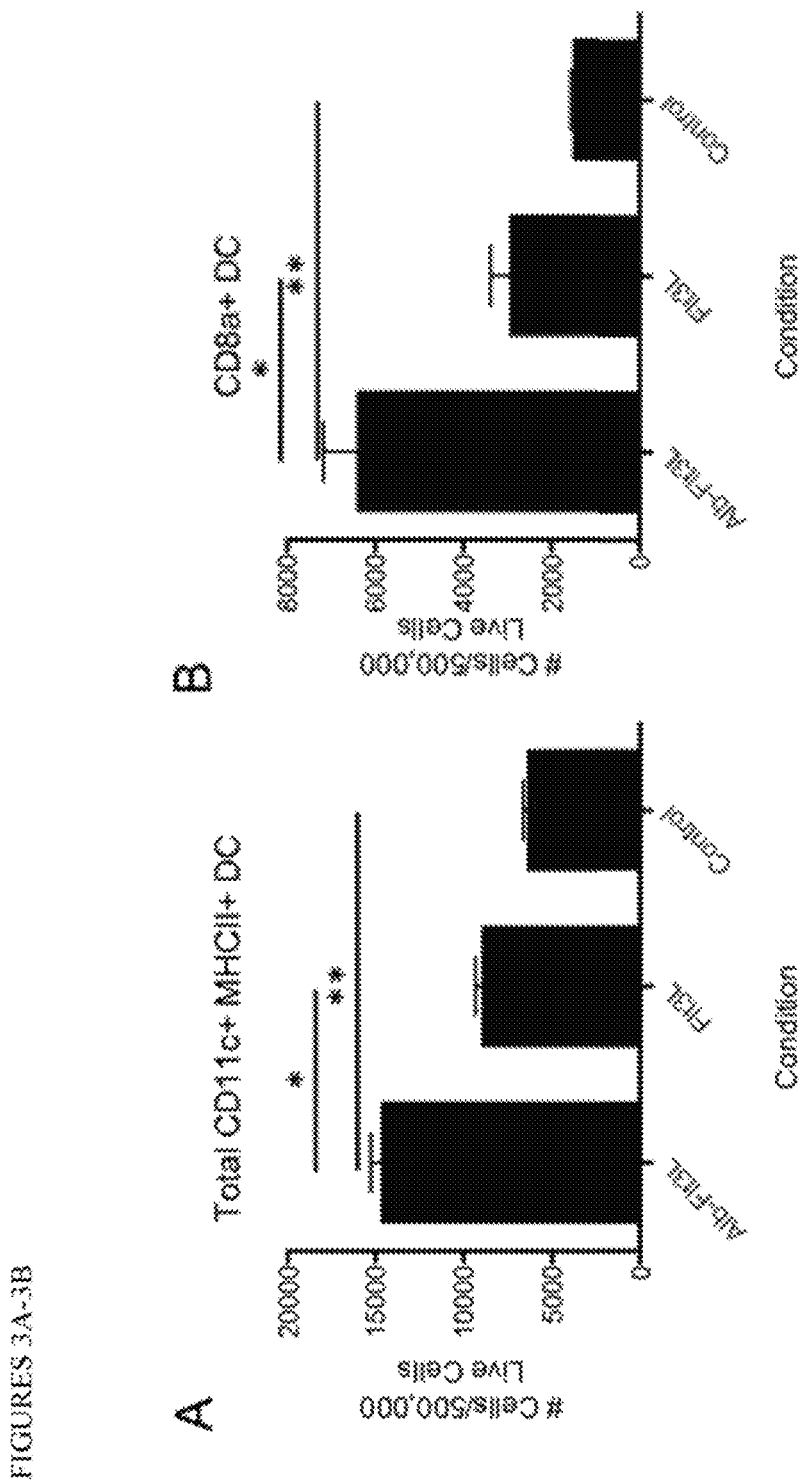
FIGS. 3A-3B. Alb-Flt3L potently expands DCs in vivo following a single injection. C57/B6 mice were injected once subcutaneously with 10 µg GM-CSF, 10 µg Flt3L, 50 µg Alb-Flt3L, or untreated. On day 5 following injection, mice were euthanized and draining lymph nodes were analyzed by flow cytometry (N=3). 3A) Alb-Flt3L (50 µg), Flt3L (10 µg), or PBS was injected into mice. DC expansion was assessed in draining LN 5 days following injection. Expansion of total DCs (CD11c+CD24+MHCII+). 3B) Expansion of cross-presenting CD8a+ DCs (CD11c+CD24+MHCII+CD8a+).

Next, we evaluated the ability of Alb-Flt3L to support cross-presenting dendritic cell expansion in vivo. Previous studies have shown that for Flt3L to mediate a significant effect on immune cell populations in vivo, daily injections were required due to the short half-life of Flt3L. Since albumin conjugation is known to significantly extend the half-life of molecules it is associated with, we tested if a single injection of Alb-Flt3L could mediate an increase in dendritic cells. C57BL/6 mice were injected with 10 μg Flt3L or 50 μg Alb-Flt3L due to its molecular weight. 5 days after cytokine injection, dLN cells were analyzed by flow cytometry. Alb-Flt3L significantly increased the frequency of the described dendritic cell populations (FIG. 3 A,B). These data indicates that Alb-Flt3L can overcome the half-life challenges of Flt3L and modulate an expansion and skewing of dendritic cell phenotypes in vivo.

Example 3

Alb-Flt3L promotes antigen specific T and B cell responses in vivo following protein immunization.

Knowing that Alb-Flt3L is able to expand cross-presenting DCs in vivo, we aimed to explore whether Alb-Flt3L treatment could enhance the immunogenicity of protein immunization. Fresh OVA protein (Sigma Aldrich, St. Louis, MO) was dissolved in PBS and 0.2 μm filtered prior to injection. On day 20 after initial injection, blood was collected in EDTA coated tubes. Samples were centrifuged and serum was collected and saved for ELISA. Remaining cells were RBC lysed and stain for flow cytometric analysis as described. 5 day prior to OVA immunization, C57BL/6 mice were injected with Flt3L or Alb-Flt3L to generate dendritic cells. For analysis of OVA specific antibody titers, high-binding ELISA plates (Genesee scientific, San Diego, CA) were coated overnight with 2 μg/ml OVA protein in 0.1M Sodium carbonate/bicarbonate buffer pH to 9.5. The following day, cells were washed using 0.05% Tween-20/PBS and blocked with 10% FBS/PBS. Serum samples were diluted from $1:10^1$-$1:10^8$ and added to ELISA plates in triplicate. Signal was detected using biotinylated antimouse IgG1 (Clone: RMG1-1) or IgG2a (Clone: RMG2a-62) and subsequent streptavidin-HRP. TMB substrate (Catalog #555214) was used to develop signal and absorbance was measured using dual measurement at 450 nm and 570 nm on an xMark plate spectrophotometer (Bio-Rad, Hercules, CA). Positive titer was set as two standard deviations above absorbance for naïve mice at a given titer.

Figure 4A:
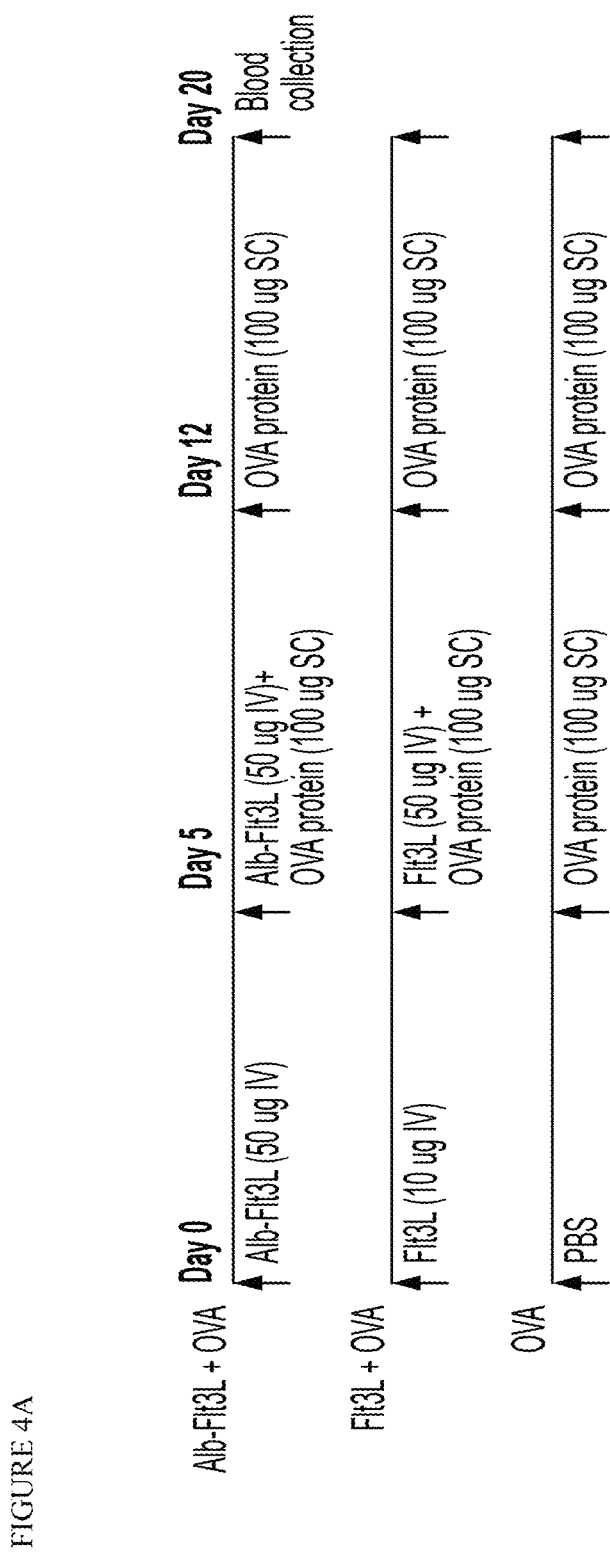
FIG. 4A is a schematic depicting experimental design including injection conditions and schedule for cytokines and OVA immunization.
Figures 4C, 4D, 4E, 4F, 4G, 4H:
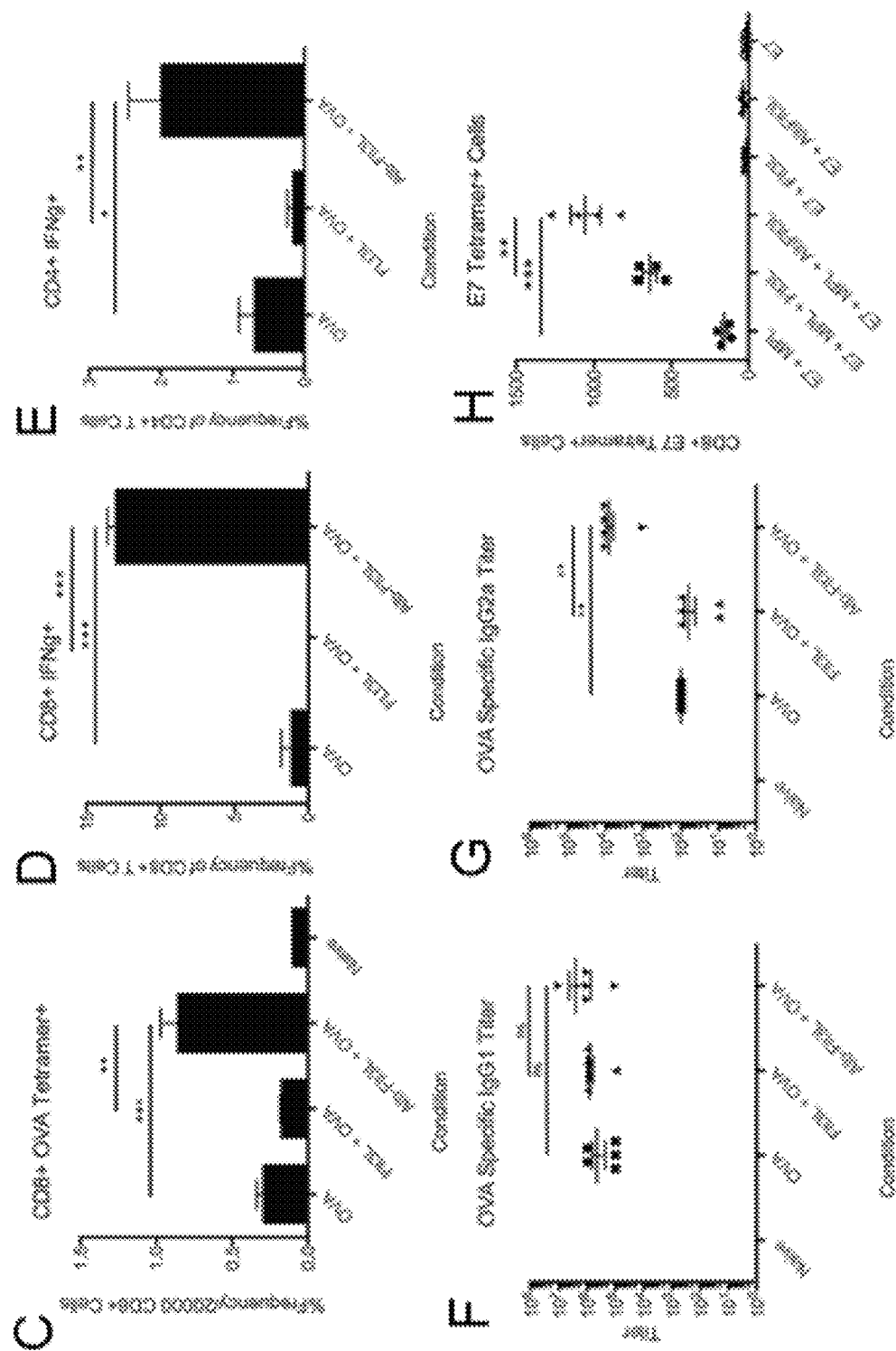
FIGS. 4C-4H. Alb-Flt3L-mediated DC expansion promotes antigen specific adaptive immune responses following protein vaccination. 4C) Alb-Flt3L (50 m), Flt3L (10 m), or PBS was injected into mice. 5 days later, cytokines were re-administered with whole OVA protein (100 m). 7 days later, OVA was re-administered. 20 days following first injection, blood was collected and immune responses measured. Percentage of CD8+OVA tetramer+ cells show, 4D) CD8+ IFNg+ cells and 4E) CD4+ IFNg+ cells following in vitro re-stimulation. OVA specific antibody titers for 4F) IgG1 and 4G) IgG2a measured by ELISA. 4H) Immunization with E7 long peptide (5 µg) with or without MPL adjuvant (10 µg) and cytokines as described in 4C following the same time course. E7 specific CD8+ cell expansion was measured by tetramer staining.

On day 5, mice were injected with Flt3L or Alb-Flt3L and immunized with OVA. 1 week later, mice were immunized with OVA alone. Blood was collected on day 20 after initial injection and analyzed for antibody responses and Th1 immunity (FIG. 4A). Mice treated with Alb-Flt3L generated the antigen specific T cell immunity as measured by intracellular cytokine staining of CD4+ and CD8+ T cells for IFNg and OVA tetramer staining (FIGS. 4 C,D,E). Mice across all treatment groups generated similar OVA specific IgG1 titers (FIG. 4F). Significantly, mice treated with Alb-Flt3L generated the strongest IgG2a antibody titer (FIG. 4G), which is known to be promoted by IFNg signaling.

To gauge responses to a different antigen system, HPV E7 was used. HPV E7aa 43-62 long peptide contains the immunodominant H-2db restricted E7 epitope which requires cross priming to generate a CD8+ T cell response. Mice were injected with Flt3L or Alb-Flt3L, followed by E7 long peptide and MPL as an adjuvant as described. 20 days after initial injection, PBMCs were analyzed for the presence of E7 specific CD8+ T cells by tetramer staining (FIG. 4B). Mice treated with Alb-Flt3L, E7 long peptide and MPL developed the highest number of E7 specific CD8+ T cells compared to other treatment groups (FIG. 4H). The results shown strongly supports the notion that Alb-Flt3L facilitates the development antigen specific T and B cell responses.

Example 4

In vivo tracking of Alb-Flt3L reveals enhanced half-life and preferential tissue accumulation in the draining lymph node and tumor with little toxicity concerns.

Fluorescently labeled cytokines were generated by labeling 1 mg of Flt3L or Alb-Flt3L with Alexa Fluor 647 NHS ester primary amine labeling kit (Invitrogen/Thermo Fisher, Waltham, MA) according to kit instructions. Following labeling, products were purified using extensive dialysis for 24 hours. Fluorescent cytokines were then injected s.c. into C57BL/6 mice. 16 hours later, mice were euthanized and tissues harvested. Subsequent imaging was performed on an IVIS spectrum in vivo imaging system (Perkin Elmer, Waltham, MA). Following IVIS imaging, draining lymph nodes (inguinal and auxiliary) were ground and single cell suspensions acquired as previously described. Cells were then stained as described and analyzed by flow cytometry.

Figure 5A:
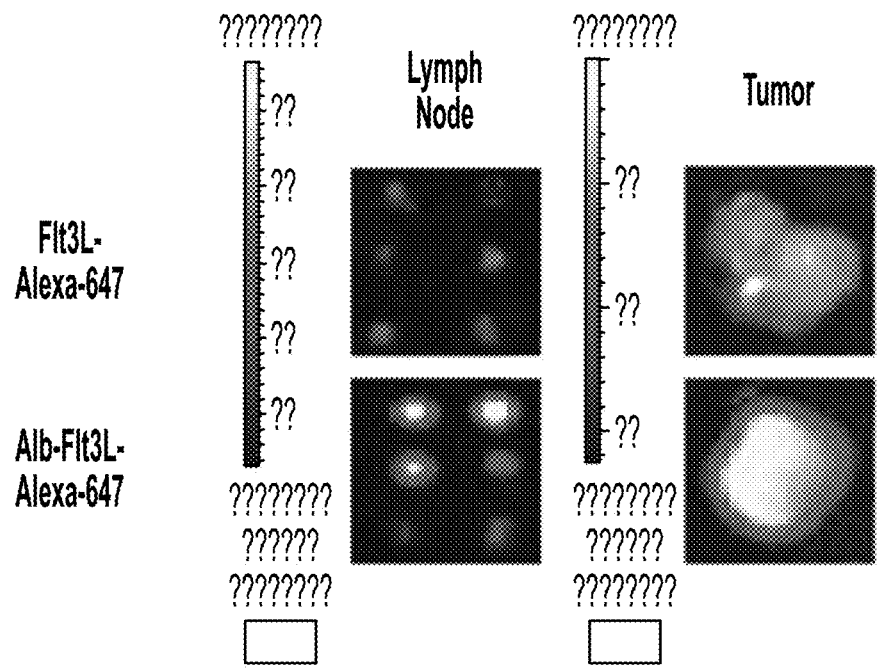
FIGS. 5A-5C. Albumin fusion promotes LN and TM accumulation and extends half-life. 5A) Alb-Flt3L (50 µg) or Flt3L (10 µg) were labeled using a commercially available Alexa-647 labeling kit and injected into mice. 16 hours later, LN and TM were harvested and imaged by IVIS. 5B) Single cell suspensions were generated and stained with cell population markers for flow cytometric analysis. Uptake of molecules by CD11c+CD11b+ cells and T cells is shown. 5C) Alb-Flt3L (50 µg) or Flt3L (10 µg) was injected into mice and blood was collected periodically to measure half-life by Flt3L ELISA.
Figure 5B:
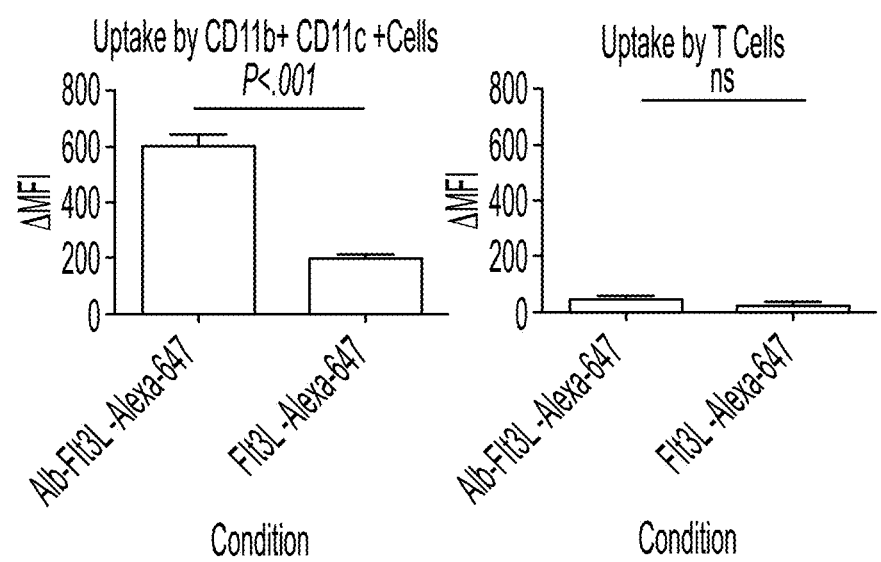
Figure 5C:
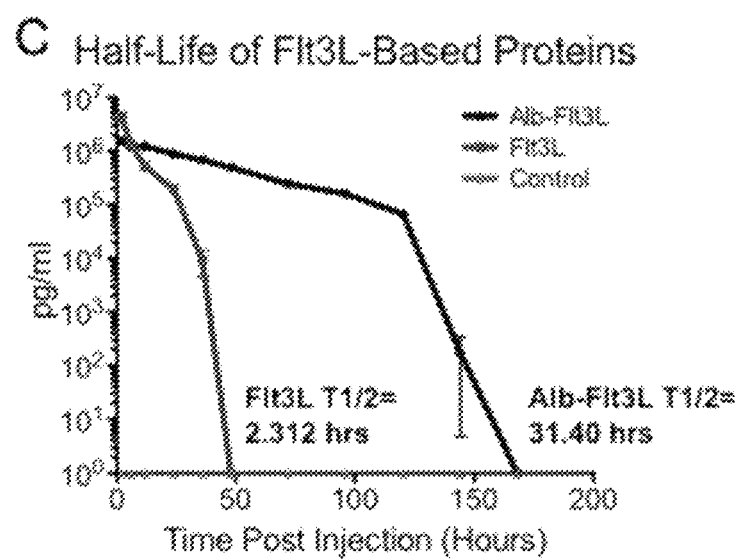
Figures 6A, 6B, 6C, 6D:
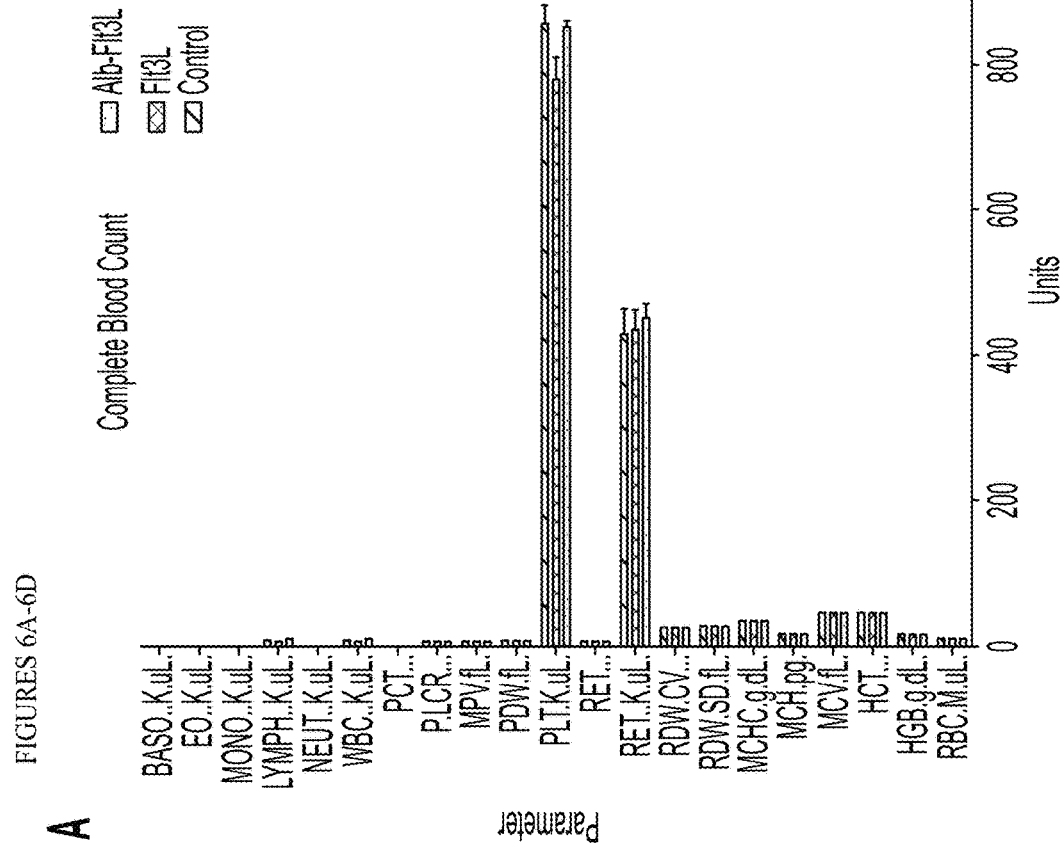
FIGS. 6A-6D show Alb-Flt3L poses little toxicity concerns measured by CBC and antibody titers. 6A) Alb-Flt3L (50 µg) or Flt3L (10 µg) was injected into mice and 5 days later, blood was collected for complete blood count. 6B) Alb-Flt3L (50 µg) or Flt3L (10 µg) was injected into mice. 7 days later, cytokines were re-administered. 20 days following initial injection, blood was collected and antibodies against 6B) Alb-Flt3L, 6C) Flt3L, or 6D) Albumin was measured by ELISA.

Surprisingly, significant signal could only be seen in the draining lymph nodes and tumor of mice injected with Alb-Flt3L compared to Flt3L (FIG. 5A). To determine which immune cells had uptaken the fluorescent cytokine, cells from the lymph nodes were stained by flow cytometry. CD11c+CD11b+ cells exhibited the most significant increase in Alexa-647 fluorescence (FIG. 5B). To determine the half-life of our Alb-Flt3L, mice were injected with 50 μg of Alb-Flt3L or 10 μg of Flt3L. Blood was collected periodically to determine circulating concentration by ELISA. Using this approach, we determined the half-life of Alb-Flt3L to be 31.4 hours compared to 2.312 hours for Flt3L, clearly indicating a significant increase (FIG. 5C).

Example 5

Administration of Alb-Flt3L promoted global antitumor immunity when combined with targeted radiation therapy in a model of HPV associated cancer and colon adenocarcinoma.

Figure 7A:
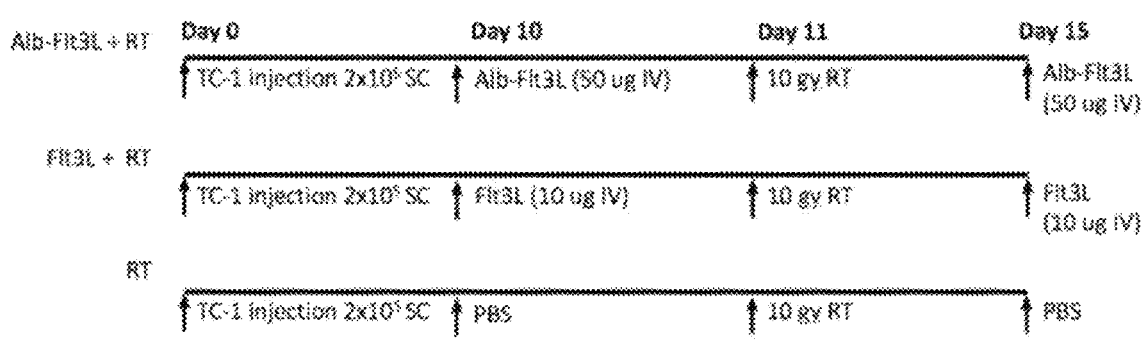
FIGS. 7A-7E show that Alb-Flt3L+ targeted radiation therapy promotes superior tumor control in TC-1 and MC38 model. 7A) A schematic diagram showing protocol: C57/B6 mice (N=5) were injected with $2\times10^5$ TC-1 tumor cells subcutaneously. 7A) Alb-Flt3L (50 µg) or Flt3L (10 µg) was injected into mice. 24 hours later, 10 gy of targeted RT was delivered using the Small Animal Radiation Research Platform (SARRP). 4 days later, cytokines were re-administered. Tumor growth and survival was measured in 7B, 7C) TC-1 model and 7D, 7E) MC38 model.
Figures 7B, 7C, 7D, 7E:
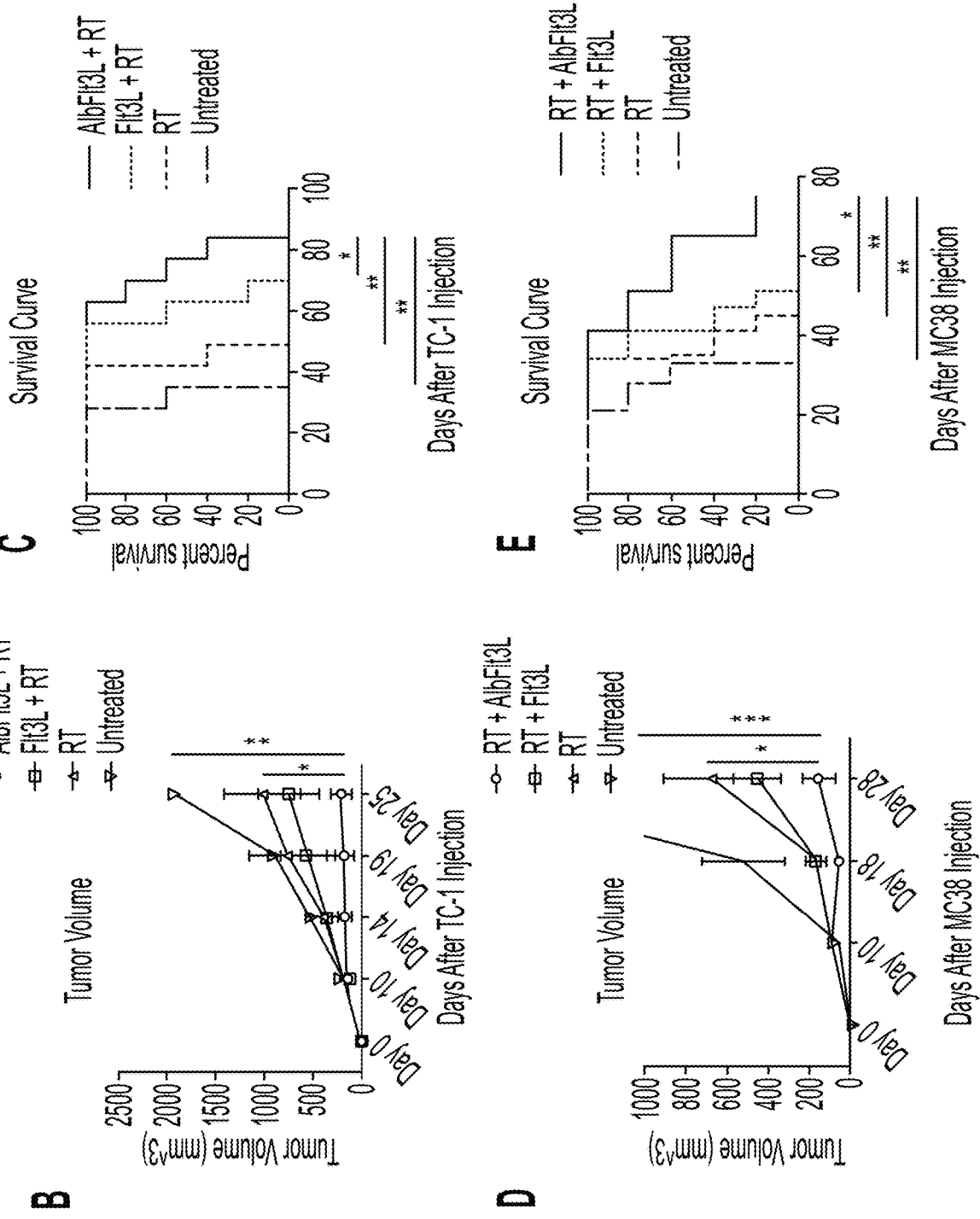
Figures 8A, 8B:
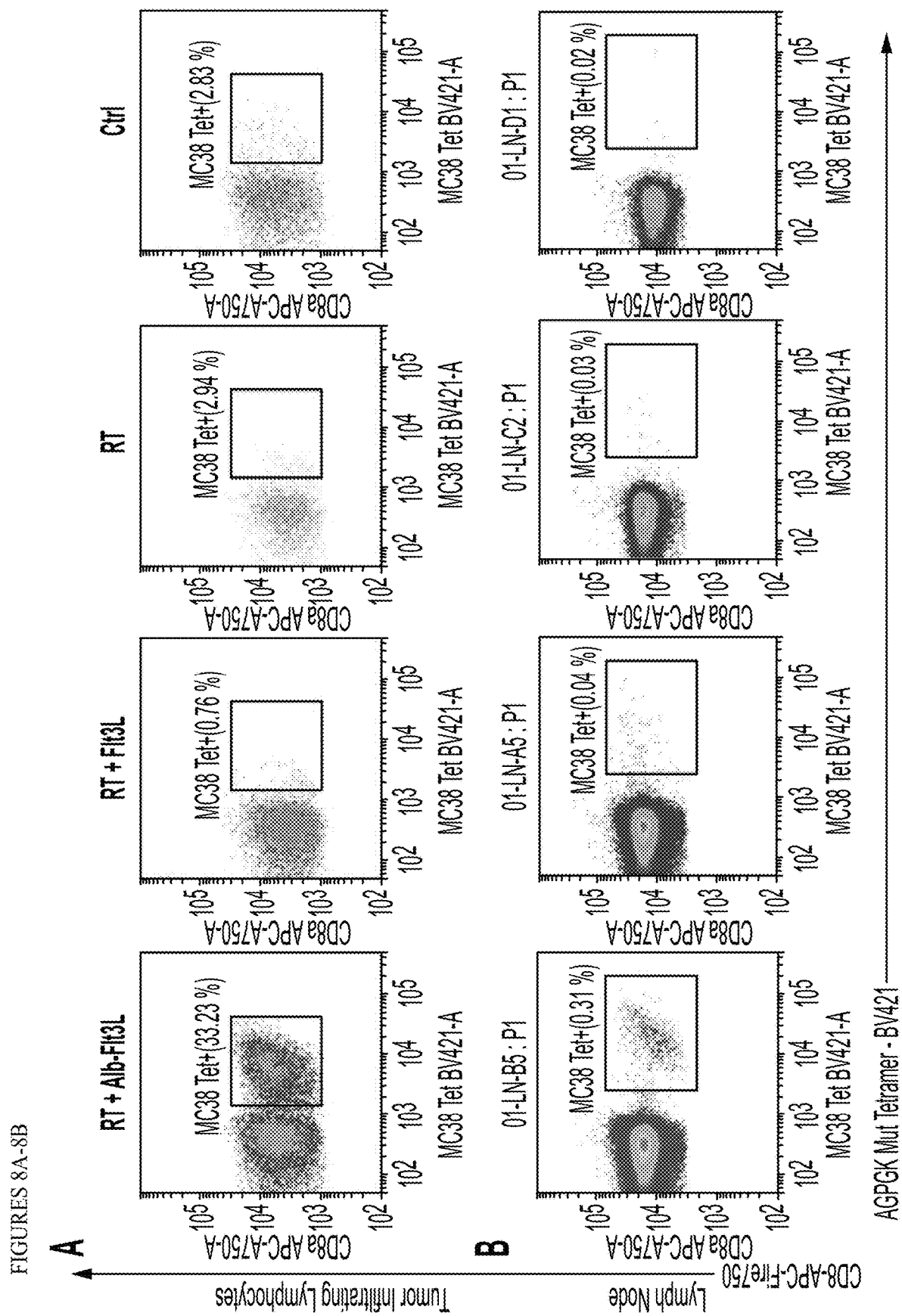
FIGS. 8A-8B show the Alb-Flt3L+ targeted radiation therapy augment neoantigen specific T cell responses without peptide vaccination in MC38 model. 8A) 25 days following treatment regimen described in FIG. 4, tumor infiltrating lymphocytes and 8B) tdLN were harvested and stained using a tetramer recognizing T cells specific for a neoantigen expressed by MC38 cells.

TC-1 cells were grown as previously described (14). $2\times10^5$ TC-1 cells were injected subcutaneously into C57BL/6 mice to form tumors. We determined whether treatment with Alb-Flt3L could augment the antitumor effect of radiation therapy in a TC1 and MC38 model. C57BL/6 mice were injected subcutaneously with $2\times10^5$ TC-1 or MC38 tumor cells. About 10 days following tumor implantation, mice were treated with Flt3L or Alb-Flt3L. The following day, 10 gy of targeted radiation therapy was administered using the small animal radiation research platform (SARRP) to prevent off target effects or disruption to draining lymph nodes while increasing tumor permeability and releasing tumor antigens. Mice were treated with an additional dose of cytokines on day 15 (FIG. 7A). As shown, treatment with Alb-Flt3L significantly improved the efficacy of radiation therapy as measured by tumor volume and overall survival in both TC-1 and MC38 model (FIGS. 7B-E). Because radiation therapy releases tumor antigen while Flt3L expanded DCs can uptake antigen and cross-present relevant peptides to CD8 T cells, this principle could prove efficacious in many types of cancer regardless of tumor tissue localization or mutations carried. We aimed to explore if our treatment regimen could uncover mutations expressed by MC38 cells and mount cytotoxic T cell responses without needing to boost these responses using peptide vaccination. Using a tetramer specific for T cells expressing TCR specific for a neoantigen expressed by MC38 cells (ADPGK mutation), we were able to see a significant expansion of neoantigen specific T cells in mice treated with radiation and Alb-Flt3L compared to controls (FIGS. 8A-B).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Topalian S L, Drake C G, Pardoll D M. (2015). Immune checkpoint blockade: a common denominator approach to 1. cancer therapy. Cancer Cell. 2015 Apr. 13; 27(4):450-61. doi: 10.1016/j.ccell.2015.03.001. Epub 2015 Apr. 6. PMID: 25858804
2. Takamori S, Toyokawa G, Takada K, Shoji F, Okamoto T, Maehara Y. (2017) Combination Therapy of Radiotherapy and Anti-PD-1/PD-L1 Treatment in Non-Small-cell Lung Cancer: A Mini-review. Clin Lung Cancer. 2017 Jul. 6. pii: 51525-7304(17)30202-4. doi: 10.1016/j.cllc.2017.06.015. [Epub ahead of print] PMID: 28739315
3. Hellmann M D, Friedman C F, Wolchok J D. (2016) Combinatorial Cancer Immunotherapies. Adv Immunol. 2016; 130:251-77. doi: 10.1016/bs.ai.2015.12.005. Epub 2016 Jan. 12. PMID: 26923003
4. Lee S J, Song L, Yang M C, Mao C P, Yang B, Yang A, Jeang J, Peng S, Wu T C, Hung C F. (2015) Local administration of granulocyte macrophage colony-stimulating factor induces local accumulation of dendritic cells and antigen-specific CD8+ T cells and enhances dendritic cell cross-presentation. Vaccine. 2015 Mar. 24; 33(13): 1549-55. doi: 10.1016/j.vaccine.2015.02.019. Epub 2015 Feb. 19. PMID: 25701675
5. Dranoff G, Jaffee E, Lazenby A, Golumbek P, Levitsky H, Brose K, Jackson V, Hamada H, Pardoll D. Mulligan R C. (1993) Vaccination with irradiated tumor cells engineered to secrete murine granulocyte-macrophage colony-stimulating factor stimulates potent, specific, and long lasting anti-tumor immunity. Proc Natl Acad Sci USA. 1993 Apr. 15; 90(8):3539-43. PMID: 8097319
6. Belz G T, Nutt S L. (2012) Transcriptional programming of the dendritic cell network. Nat Rev Immunol. 2012 Jan. 25; 12(2):101-13. doi: 10.1038/nri3149. PMID: 22273772
7. Gardner A, Ruffell B. (2016). Dendritic Cells and Cancer Immunity. Trends Immunol. 2016 December; 37(12):855-865. doi: 10.1016/j.it.2016.09.006. Epub 2016 Oct. 25. PMID: 27793569
8. Gibbons Johnson R M, Dong H. (2017) Functional Expression of Programmed Death-Ligand 1 (B7-H1) by Immune Cells and Tumor Cells. Front Immunol. 2017 Aug. 10; 8:961. doi: 10.3389/fimmu.2017.00961. eCollection 2017. PMID: 28848559
9. Pulendran B, Smith J L, Caspary G, Brasel K, Pettit D, Marakovsky E, Maliskewski C R. (1999) Distinct dendritic cell subsets differentially regulate the class of immune response in vivo. Proc Natl Acad Sci USA. 1999 Feb. 2; 96(3):1036-41. PMID: 9927689
10. Salmon H, Idoyaga J, Rahman A, Leboeuf M, Remark R, Jordan S, Casanova-Acebes M, Khudoynazarova M, Agudo J, Tung N, Chakarov S, Rivera C, Hogstad B, Bosenberg M, Hasimoto D, Gnjatic S, Bhardwaj N, Palucka A K, Brown B D, Brody J, Ginhoux F, Merad M. (2016) Expansion and Activation of CD103(+) Dendritic Cell Progenitors at the Tumor Site Enhances Tumor Responses to Therapeutic PD-L1 and BRAF Inhibition. Immunity. 2016 Apr. 19; 44(4):924-38. doi: 10.1016/j.immuni.2016.03.012. PMID: 27096321
11. Schmidt E G W, Hvam M L, Antunes F, Cameron J, Viuff D, Andersen B, Kristensen N N, Howard K A. (2017) Direct demonstration of a neonatal Fc receptor (FcRn)-driven endosomal sorting pathway for cellular recycling of albumin. J Biol Chem. 2017 Aug. 11; 292(32):13312-13322. doi: 10.1074/jbc.M117.794248. Epub 2017 Jun. 21. PMID: 28637874
12. Wang Y, Lang L, Huang P, Wang Z, Jacobson O, Kiesewette D O, Ali I U, Teng G, Niu G, Chen X. (2015) In vivo albumin labeling and lymphatic imaging. Proc Natl Acad Sci USA. 2015 Jan. 6; 112(1):208-13. doi: 10.1073/pnas.1414821112. Epub 2014 Dec. 22. PMID: 25535368
13. Inaba K, Inaba M, Romani N, Aya H, Deguchi M, Ikehara S, Muramatsu S, Steinman R M. (1992) Generation of large numbers of dendritic cells from mouse bone marrow cultures supplemented with granulocyte/macrophage colony-stimulating factor. J Exp Med. 1992 Dec. 1; 176(6):1693-702. PMID: 1460426
14. Lin K Y, Guarnieri F G, Staveley-O'Carroll K F, Levitsky H I, August J T, Pardoll D M, Wu T C. (1996) Treatment of established tumors with a novel vaccine that enhances major histocompatibility class II presentation of tumor antigen. Cancer Res. 1996 Jan. 1; 56(1):21-6. PMID: 8548765

The invention claimed is:

1. A method of treating cancer in a mammalian subject in need thereof, comprising:
   administering to the mammalian subject an effective amount of a composition comprising a polypeptide comprising albumin protein linked to a FMS-like tyrosine kinase 3 ligand (Flt3L) protein comprising a sequence having at least 80% identity to SEQ ID NO: 1, to thereby treat the cancer in the mammalian subject.

2. The method of claim 1, wherein the method further comprises administering to the mammalian subject an effective amount of at least one additional chemotherapeutic agent.

3. The method of claim 1, wherein the method further comprises administering to the mammalian subject an effective amount of an immunotherapeutic agent.

4. The method of claim 3, wherein the immunotherapeutic agent is a PD-1 inhibitor.

5. The method of claim 1, wherein the method further comprises administering to the mammalian subject an effective amount of radiation therapy.

6. The method of claim 5, wherein the radiation therapy is focused radiation therapy.

7. The method of claim 6, wherein the amount of radiation given is between about 1 gy to about 30 gy.

8. The method of claim 5 wherein the mammalian subject is suffering from human papilloma virus associated cancer.

9. The method of claim 5 wherein the mammalian subject is suffering from colon adenocarcinoma.

10. The method of claim 1, wherein the albumin protein is human.

11. The method of claim 1, wherein the Flt3L protein is human.

12. The method of claim 1 wherein the polypeptide comprises a sequence having at least 90% identity to the amino acid sequence of SEQ ID NO: 1.

13. The method of claim 1 wherein the polypeptide comprises a sequence having at least 98% identity to the amino acid sequence of SEQ ID NO: 1.

14. The method of claim 1 wherein the polypeptide comprises the amino acid sequence of SEQ ID NO: 1.

15. The method of claim 1 wherein the mammalian subject is suffering from human papilloma virus associated cancer.

16. The method of claim 1 wherein the mammalian subject is suffering from colon adenocarcinoma.

17. A method of treating cancer in a mammalian subject in need thereof, comprising: administering to the mammalian subject an effective amount of a composition comprising a polypeptide comprising albumin protein linked to a FMS-like tyrosine kinase 3 ligand (Flt3L) protein, to thereby treat the cancer in the mammalian subject, and wherein the albumin protein is murine.

18. The method of claim 17 wherein the Flt3L protein is murine.

19. The method of claim 17 wherein the polypeptide comprises the amino acid sequence of SEQ ID NO: 2.

20. The method of claim 17 wherein the polypeptide comprises the amino acid sequence of SEQ ID NO: 3.

* * * * *